(12) United States Patent
Matov et al.

(10) Patent No.: US 11,771,526 B2
(45) Date of Patent: Oct. 3, 2023

(54) SYSTEMS AND METHODS FOR NONLINEAR TOOTH MODELING

(71) Applicant: Align Technology, Inc., San Jose, CA (US)

(72) Inventors: Vadim Matov, San Jose, CA (US); Sergei Brodsky, San Jose, CA (US); Bastien Pesenti, San Jose, CA (US); Yuri Syrov, San Jose, CA (US); Ping Tang, Milpitas, CA (US); Manlio Fabio Valdivieso Casique, Santa Clara, CA (US); Olga Matusevich, Moscow (RU); Igor Kvasov, Los Altos, CA (US)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 17/949,113

(22) Filed: Sep. 20, 2022

(65) Prior Publication Data
US 2023/0126690 A1 Apr. 27, 2023

Related U.S. Application Data

(63) Continuation of application No. 16/730,865, filed on Dec. 30, 2019, now Pat. No. 11,478,334.

(60) Provisional application No. 62/788,025, filed on Jan. 3, 2019.

(51) Int. Cl.
*A61C 7/00* (2006.01)
*A61C 7/08* (2006.01)
*G16H 20/00* (2018.01)
*G06T 17/20* (2006.01)

(52) U.S. Cl.
CPC .............. *A61C 7/002* (2013.01); *A61C 7/08* (2013.01); *G06T 17/20* (2013.01); *G16H 20/00* (2018.01); *G06T 2207/30036* (2013.01)

(58) Field of Classification Search
CPC .......... A61C 7/002; A61C 7/08; G06T 17/20; G06T 2207/30036; G16H 20/00
See application file for complete search history.

(56) References Cited

U.S. PATENT DOCUMENTS

| | | | |
|---|---|---|---|
| 6,227,850 B1 | 5/2001 | Chishti et al. | |
| 6,227,851 B1 | 5/2001 | Chishti et al. | |
| 6,299,440 B1 | 10/2001 | Phan et al. | |
| 6,318,994 B1 | 11/2001 | Chishti et al. | |
| 6,371,761 B1 | 4/2002 | Cheang et al. | |

(Continued)

*Primary Examiner* — Molly Wilburn
(74) *Attorney, Agent, or Firm* — Wilson Sonsini Goodrich & Rosati

(57) ABSTRACT

Systems and methods of generating an orthodontic model are disclosed. The method may include: generating an initial model of a patient dentition; generating a target model of the patient dentition; defining a plurality of caps and a plurality of links, wherein each link connects two of the plurality of caps; generating a relaxed model of a dental appliance from the plurality of caps and the plurality of links; generating a deformed model of a dental appliance from the plurality of caps and plurality of links; and determining a plurality of movements, wherein the plurality of moments transform the relaxed model to the deformed model and wherein the moments are configured to direct the patient dentition from the initial model to the target model.

18 Claims, 14 Drawing Sheets

(56) References Cited

U.S. PATENT DOCUMENTS

| | | |
|---|---|---|
| 6,386,878 B1 | 5/2002 | Pavlovskaia et al. |
| 6,406,292 B1 | 6/2002 | Chishti et al. |
| 6,409,504 B1 | 6/2002 | Jones et al. |
| 6,457,972 B1 | 10/2002 | Chishti et al. |
| 6,488,499 B1 | 12/2002 | Miller |
| 6,514,074 B1 | 2/2003 | Chishti et al. |
| 6,582,229 B1 | 6/2003 | Miller et al. |
| 6,602,070 B2 | 8/2003 | Miller et al. |
| 6,621,491 B1 | 9/2003 | Baumrind et al. |
| 6,688,886 B2 | 2/2004 | Hughes et al. |
| 6,726,478 B1 | 4/2004 | Isiderio et al. |
| 6,729,876 B2 | 5/2004 | Chishti et al. |
| 6,739,869 B1 | 5/2004 | Taub et al. |
| 6,767,208 B2 | 7/2004 | Kaza |
| 6,783,360 B2 | 8/2004 | Chishti |
| 7,040,896 B2 | 5/2006 | Pavlovskaia et al. |
| 7,063,532 B1 | 6/2006 | Jones et al. |
| 7,074,038 B1 | 7/2006 | Miller |
| 7,074,039 B2 | 7/2006 | Kopelman et al. |
| 7,077,647 B2 | 7/2006 | Choi et al. |
| 7,108,508 B2 | 9/2006 | Hedge et al. |
| 7,134,874 B2 | 11/2006 | Chishti et al. |
| 7,156,661 B2 | 1/2007 | Choi et al. |
| 7,160,107 B2 | 1/2007 | Kopelman et al. |
| 7,241,142 B2 | 7/2007 | Abolfathi et al. |
| 7,293,988 B2 | 11/2007 | Wen |
| 7,309,230 B2 | 12/2007 | Wen |
| 7,357,634 B2 | 4/2008 | Knopp |
| 7,555,403 B2 | 6/2009 | Kopelman et al. |
| 7,637,740 B2 | 12/2009 | Knopp |
| 7,689,398 B2 | 3/2010 | Cheng et al. |
| 7,736,147 B2 | 6/2010 | Kaza et al. |
| 7,746,339 B2 | 6/2010 | Matov et al. |
| 7,844,356 B2 | 11/2010 | Matov et al. |
| 7,844,429 B2 | 11/2010 | Matov et al. |
| 7,865,259 B2 | 1/2011 | Kuo et al. |
| 7,878,804 B2 | 2/2011 | Korytov et al. |
| 7,880,751 B2 | 2/2011 | Kuo et al. |
| 7,904,308 B2 | 3/2011 | Arnone et al. |
| 7,930,189 B2 | 4/2011 | Kuo |
| 7,942,672 B2 | 5/2011 | Kuo |
| 7,970,627 B2 | 6/2011 | Kuo et al. |
| 7,970,628 B2 | 6/2011 | Kuo et al. |
| 8,038,444 B2 | 10/2011 | Kitching et al. |
| 8,044,954 B2 | 10/2011 | Kitching et al. |
| 8,075,306 B2 | 12/2011 | Kitching et al. |
| 8,092,215 B2 | 1/2012 | Stone-Collonge et al. |
| 8,099,268 B2 | 1/2012 | Kitching et al. |
| 8,108,189 B2 | 1/2012 | Chelnokov et al. |
| 8,126,726 B2 | 2/2012 | Matov et al. |
| 8,260,591 B2 | 9/2012 | Kass et al. |
| 8,275,180 B2 | 9/2012 | Kuo |
| 8,401,826 B2 | 3/2013 | Cheng et al. |
| 8,439,672 B2 | 5/2013 | Matov et al. |
| 8,562,338 B2 | 10/2013 | Kitching et al. |
| 8,591,225 B2 | 11/2013 | Wu et al. |
| 8,788,285 B2 | 7/2014 | Kuo |
| 8,843,381 B2 | 9/2014 | Kuo et al. |
| 8,874,452 B2 | 10/2014 | Kuo |
| 8,896,592 B2 | 11/2014 | Boltunov et al. |
| 8,930,219 B2 | 1/2015 | Trosien et al. |
| 9,037,439 B2 | 5/2015 | Kuo et al. |
| 9,060,829 B2 | 6/2015 | Sterental et al. |
| 9,125,709 B2 | 9/2015 | Matty |
| 9,211,166 B2 | 12/2015 | Kuo et al. |
| 9,220,580 B2 | 12/2015 | Borovinskih et al. |
| 9,364,296 B2 | 6/2016 | Kuo |
| 9,375,300 B2 | 6/2016 | Matov et al. |
| 9,414,897 B2 | 8/2016 | Wu et al. |
| 9,492,245 B2 | 11/2016 | Sherwood et al. |
| 9,642,678 B2 | 5/2017 | Kuo |
| 10,248,883 B2 | 4/2019 | Borovinskih et al. |
| 10,342,638 B2 | 7/2019 | Kitching et al. |
| 10,463,452 B2 | 11/2019 | Matov et al. |
| 10,595,966 B2 | 3/2020 | Carrier, Jr. et al. |
| 10,617,489 B2 | 4/2020 | Grove et al. |
| 10,722,328 B2 | 7/2020 | Velazquez et al. |
| 10,758,322 B2 | 9/2020 | Pokotilov et al. |
| 10,779,718 B2 | 9/2020 | Meyer et al. |
| 10,792,127 B2 | 10/2020 | Kopelman et al. |
| 10,828,130 B2 | 11/2020 | Pokotilov et al. |
| 10,835,349 B2 | 11/2020 | Cramer et al. |
| 10,881,486 B2 * | 1/2021 | Wen .................. A61C 7/08 |
| 10,973,611 B2 | 4/2021 | Pokotilov et al. |
| 10,980,613 B2 * | 4/2021 | Shanjani ............ G02B 27/0172 |
| 10,996,813 B2 | 5/2021 | Makarenkova et al. |
| 10,997,727 B2 | 5/2021 | Xue et al. |
| 11,013,581 B2 * | 5/2021 | Sabina .................. A61C 7/002 |
| 11,020,205 B2 | 6/2021 | Li et al. |
| 11,020,206 B2 | 6/2021 | Shi et al. |
| 11,026,766 B2 | 6/2021 | Chekh et al. |
| 11,033,359 B2 | 6/2021 | Velazquez et al. |
| 11,071,608 B2 | 7/2021 | Derakhshan et al. |
| 11,096,763 B2 | 8/2021 | Akopov et al. |
| 11,116,605 B2 | 9/2021 | Nyukhtikov et al. |
| 11,147,652 B2 | 10/2021 | Mason et al. |
| 11,151,753 B2 | 10/2021 | Gao et al. |
| 11,154,381 B2 | 10/2021 | Roschin et al. |
| 11,259,896 B2 | 3/2022 | Matov et al. |
| 11,357,598 B2 | 6/2022 | Cramer |
| 11,395,717 B2 | 7/2022 | Yuryev et al. |
| 11,432,908 B2 | 9/2022 | Kopelman et al. |
| 11,464,604 B2 | 10/2022 | Makarenkova et al. |
| 11,478,334 B2 * | 10/2022 | Matov .................. A61C 7/002 |
| 11,484,389 B2 | 11/2022 | Sterental et al. |
| 11,521,732 B2 | 12/2022 | Levin et al. |
| 11,534,272 B2 | 12/2022 | Li et al. |
| 11,553,988 B2 | 1/2023 | Mednikov et al. |
| 11,633,268 B2 | 4/2023 | Moalem et al. |
| 2003/0008259 A1 | 1/2003 | Kuo et al. |
| 2003/0143509 A1 | 7/2003 | Kopelman et al. |
| 2003/0207227 A1 | 11/2003 | Abolfathi |
| 2004/0137400 A1 | 7/2004 | Chishti et al. |
| 2004/0152036 A1 | 8/2004 | Abolfathi |
| 2004/0197728 A1 | 10/2004 | Abolfathi et al. |
| 2004/0259049 A1 | 12/2004 | Kopelman et al. |
| 2005/0182654 A1 | 8/2005 | Abolfathi et al. |
| 2005/0244791 A1 | 11/2005 | Davis et al. |
| 2006/0127836 A1 | 6/2006 | Wen |
| 2006/0127852 A1 | 6/2006 | Wen |
| 2006/0127854 A1 | 6/2006 | Wen |
| 2006/0275731 A1 | 12/2006 | Wen et al. |
| 2006/0275736 A1 | 12/2006 | Wen et al. |
| 2008/0306724 A1 | 12/2008 | Kitching et al. |
| 2010/0009308 A1 | 1/2010 | Wen et al. |
| 2010/0068672 A1 | 3/2010 | Arjomand et al. |
| 2010/0068676 A1 | 3/2010 | Mason et al. |
| 2010/0092907 A1 | 4/2010 | Knopp |
| 2010/0167243 A1 | 7/2010 | Spiridonov et al. |
| 2013/0204599 A1 | 8/2013 | Matov et al. |
| 2016/0095668 A1 * | 4/2016 | Kuo .................. A61C 7/00 703/6 |
| 2016/0310235 A1 | 10/2016 | Derakhshan et al. |
| 2017/0273760 A1 | 9/2017 | Morton et al. |
| 2018/0189434 A1 * | 7/2018 | Zhou .................. A61C 7/002 |
| 2018/0280118 A1 | 10/2018 | Cramer |
| 2019/0321135 A1 * | 10/2019 | Wen .................. A61C 7/08 |
| 2019/0328487 A1 | 10/2019 | Levin et al. |
| 2019/0328488 A1 | 10/2019 | Levin et al. |
| 2020/0107915 A1 | 4/2020 | Roschin et al. |
| 2020/0155274 A1 | 5/2020 | Pimenov et al. |
| 2020/0297458 A1 | 9/2020 | Roschin et al. |
| 2020/0306011 A1 | 10/2020 | Chekhonin et al. |
| 2020/0306012 A1 | 10/2020 | Roschin et al. |
| 2020/0360109 A1 | 11/2020 | Gao et al. |
| 2021/0073998 A1 | 3/2021 | Brown et al. |
| 2021/0134436 A1 | 5/2021 | Meyer et al. |
| 2021/0174477 A1 | 6/2021 | Shi et al. |

* cited by examiner

SYSTEMS AND METHODS FOR NONLINEAR TOOTH MODELING

CROSS-REFERENCE

This application is a continuation of U.S. application Ser. No. 16/730,865, filed Dec. 30, 2019, now U.S. Pat. No. 11,478,334, issued Oct. 25, 2022, which claims the benefit of U.S. Provisional Application No. 62/788,025, filed Jan. 3, 2019, which applications are incorporated herein by reference.

TECHNICAL FIELD

The technical field generally relates to system and methods of correcting malocclusions of teeth. More particularly, the technical field relates to system and methods of accurately and realistically generating models of tooth force systems, and systems and methods of determining clinically effective orthodontic aligners for teeth.

BACKGROUND

Existing methods for orthodontic modeling of forces and moments may be time consuming, computationally expensive, and/or inaccurate. Methods of modeling forces and modeling based on finite element analysis may suffer from non-convergence and/or excessive time consumption.

SUMMARY

The present disclosure addresses technical needs for fast and accurate models of force and/or moment systems to predict the effects of treatment plans and design/manufacture effective dental appliances. When designing and/or manufacturing dental appliances, such as aligners, it may be useful to optimize the position(s) and/or orientation(s) of portions of the dental appliances. Doing so may ensure comfort (e.g., dental appliances are fitting as intended) and more accurate implementation of various functionalities (e.g., that force systems and/or torques applied as part of a treatment plan are being applied as intended). The implementations described herein may accurately calculate force systems (forces, torques, etc.) of dental appliances by modeling the regions that surround a specific tooth/teeth as "caps" and modeling various translational and/or rotational relationships between caps. In some implementations, relaxed and/or deformed models of a dental appliance are identified and used to map force(s)/torque(s) between caps and/or links. Techniques described herein may be useful to design/manufacture dental appliances that call for application of complex and/or non-linear force(s)/torque(s) on a patient's dentition.

A computer-implemented method of generating an orthodontic model of tooth movements is disclosed. The computer-implemented method my comprise generating an initial model of a patient dentition, the initial three-dimensional model comprising a first, three-dimensional representation of the patient dentition at a stage of a treatment plan, generating a target model of the patient dentition, the target three-dimensional model comprising a second, three-dimensional representation of the patient dentition after the stage of the treatment plan, defining a plurality of caps and a plurality of links, wherein each cap of the plurality of caps represents a set of contact points on a tooth of the dentition, and wherein each link of the plurality of links represents a connection between two of the plurality of caps, generating a relaxed model of a dental appliance from the plurality of caps and the plurality of links, the relaxed model of the dental appliance representing physical properties of the dental appliance at a first state, generating a deformed model of a dental appliance from the plurality of caps and plurality of links, the deformed model of the dental appliance representing the physical properties of the dental appliance at a second state corresponding to a use of the dental appliance, determining a plurality of transformational parameters, wherein the plurality of transformational parameters transform the relaxed model to the deformed model and wherein the plurality of transformational parameters are configured to direct the patient dentition from the initial model to the target model, and using the plurality of transformation parameters to design the dental appliance.

In some embodiments, the plurality of transformation parameters comprise one or more of a plurality of forces and a plurality of moments.

In some embodiments, the computer implemented method may include mapping the relaxed model onto the deformed model or expressing the relaxed model and the deformed model in an elastic coordinate system.

In some embodiments, the computer implemented method may include determining a force system for each pair of teeth. The method may also include summing the force system for each pair to determine a total force for a whole arch system.

In some embodiments, the computer implemented method may include determining a moment system for each pair of teeth. The method may also include summing the moment system for each pair to determine a total moment for a whole arch system.

In some embodiments, a whole arch system has no total force or total moment.

In some embodiments, the initial model of patient dentition comprises a scan of the patient dentition or a mold of the patient dentition. Each of the plurality of caps may include a reduced dimensional surface which represents the patient dentition. Each of the plurality of links may include a Hookian stiffness parameter.

In some embodiments, the method may include repeating the determining a plurality of moments for a second stage in the treatment plan.

In some embodiments, the method may include fabricating one or a plurality of dental appliances.

In some embodiments, the method reduces a time to generate a force model by 10% relative solid model analysis.

In some embodiments, the method includes creating or developing the treatment plan based on the plurality of moments or determining an effectiveness of the treatment plan based on the plurality of moments.

In some embodiments, the method includes creating a plurality of treatment plans based on the plurality of moments and selecting a target treatment plan from the plurality of treatment plans.

In some embodiments, the selecting a target treatment plan is based on a time efficiency of the target treatment plan. In some embodiments, the selecting a target treatment plan is based on a therapeutic effectiveness of the target treatment plan.

In some embodiments, the determining a plurality of tooth moments is performed "chair side".

A computer-implemented method of generating an orthodontic treatment plan is also disclosed. The method may include generating an initial model of a patient dentition, the initial three-dimensional model comprising a first, three-dimensional representation of the patient dentition at a stage of a treatment plan, generating a target model of the patient dentition, the target three-dimensional model comprising a second, three-dimensional representation of the patient dentition after the stage of the treatment plan, defining a plurality of caps and a plurality of links, wherein each cap of the plurality of caps represents a set of contact points on a tooth of the dentition, and wherein each link of the plurality of links represents a connection between two of the plurality of caps, generating a relaxed model of a dental appliance from the plurality of caps and the plurality of links, the relaxed model of the dental appliance representing physical properties of the dental appliance at a first state, generating a deformed model of a dental appliance from the plurality of caps and plurality of links, the deformed model of the dental appliance representing the physical properties of the dental appliance at a second state corresponding to a use of the dental appliance, determining a plurality of transformational parameters, wherein the plurality of transformational parameters transform the relaxed model to the deformed model and wherein the plurality of transformational parameters are configured to direct the patient dentition from the initial model to the target model, using the plurality of transformation parameters to design the dental appliance, and providing the dental appliance to a patient.

A system for generating an orthodontic treatment plan is disclosed. The system may include memory storing computer-program instructions one or more physical processors coupled to the memory, the one or more physical processors configured to implement a computer-implemented method using the computer-program instructions, the computer-implemented method generating a virtual depiction of an orthodontic treatment of a patient, the computer-implemented method comprising: generating an initial model of a patient dentition, the initial three-dimensional model comprising a first, three-dimensional representation of the patient dentition at a stage of a treatment plan, generating a target model of the patient dentition, the target three-dimensional model comprising a second, three-dimensional representation of the patient dentition after the stage of the treatment plan, defining a plurality of caps and a plurality of links, wherein each cap of the plurality of caps represents a set of contact points on a tooth of the dentition, and wherein each link of the plurality of links represents a connection between two of the plurality of caps, generating a relaxed model of a dental appliance from the plurality of caps and the plurality of links, the relaxed model of the dental appliance representing physical properties of the dental appliance at a first state, generating a deformed model of a dental appliance from the plurality of caps and plurality of links, the deformed model of the dental appliance representing the physical properties of the dental appliance at a second state corresponding to a use of the dental appliance, determining a plurality of transformational parameters, wherein the plurality of transformational parameters transform the relaxed model to the deformed model and wherein the plurality of transformational parameters are configured to direct the patient dentition from the initial model to the target model, and using the plurality of transformation parameters to design the dental appliance.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1A:
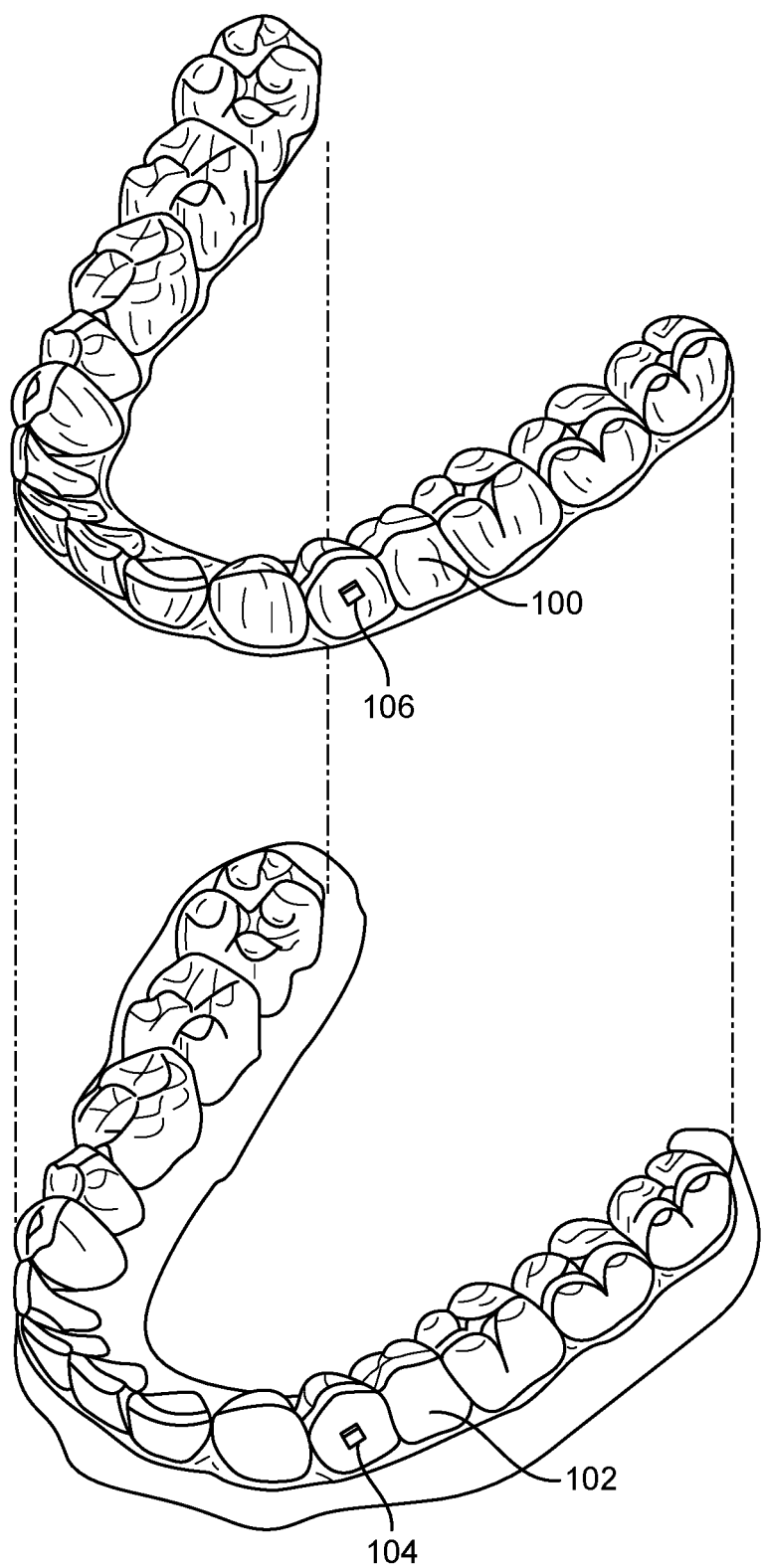
FIG. 1A illustrates a tooth repositioning appliance, in accordance with one or more embodiments herein.

A better understanding of the features and advantages of the present disclosure will be obtained by reference to the following detailed description that sets forth illustrative embodiments, in which the principles of embodiments of the present disclosure are utilized, and the accompanying drawings.

Although the detailed description contains many specifics, these should not be construed as limiting the scope of the disclosure but merely as illustrating different examples and aspects of the present disclosure. It should be appreciated that the scope of the disclosure includes other embodiments not discussed in detail above. Various other modifications, changes and variations which will be apparent to those skilled in the art may be made in the arrangement, operation and details of the methods, systems, and apparatus of the present disclosure provided herein without departing from the spirit and scope of the invention as described herein.

As used herein the terms "dental appliance," and "tooth receiving appliance" are treated synonymously. As used herein, a "dental positioning appliance" or an "orthodontic appliance" may be treated synonymously, and may include any dental appliance configured to change the position of a patient's teeth in accordance with a plan, such as an orthodontic treatment plan. A "dental positioning appliance" or "orthodontic appliance," as used herein, may include a set of dental appliances configured to incrementally change the position of a patient's teeth over time. As noted herein, dental positioning appliances and/or orthodontic appliances may comprise polymeric appliances configured to move a patient's teeth in accordance with an orthodontic treatment plan.

As used herein the term "and/or" may be used as a functional word to indicate that two words or expressions are to be taken together or individually. For example, the phrase "A and/or B" encompasses A alone, B alone, and A and B together. Depending on context, the term "or" need not exclude one of a plurality of words/expressions. As an example, the phrase "A or B" need not exclude A and B together.

As used herein the terms "torque" and "moment" are treated synonymously.

As used herein a "moment" may encompass a force acting on an object such as a tooth at a distance from a center of resistance. The moment may be calculated with a vector cross product of a vector force applied to a location corresponding to a displacement vector from the center of resistance, for example. The moment may comprise a vector pointing in a direction. A moment opposing another moment may encompass one of the moment vectors oriented toward a first side of the object such as the tooth and the other moment vector oriented toward an opposite side of the object such as tooth, for example. Any discussion herein referring to application of forces on a patient's teeth is equally applicable to application of moments on the teeth, and vice-versa.

As used herein a "plurality of teeth" may encompass two or more teeth. A plurality of teeth may, but need not, comprise adjacent teeth. In some embodiments, one or more posterior teeth comprises one or more of a molar, a premolar or a canine, and one or more anterior teeth comprising one or more of a central incisor, a lateral incisor, a cuspid, a first bicuspid or a second bicuspid.

The embodiments disclosed herein may be well suited for moving one or more teeth of the first group of one or more teeth or moving one or more of the second group of one or more teeth, and combinations thereof.

Systems and Methods for Determining Tooth Transformational Parameters Based on a Nonlinear Model Systems and methods of the present disclosure provide an orthodontic model of tooth moments. In some examples the method may comprise generating an initial model of a patient dentition, the initial three-dimensional model comprising a first, three-dimensional representation of the patient dentition at a stage of a treatment plan. In some examples, the methods herein may comprise generating a target model of the patient dentition, the target three-dimensional model comprising a second, three-dimensional representation of the patient dentition after the stage of the treatment plan.

In some examples the method may comprise defining a plurality of caps and a plurality of links to model application of a force system to be applied according to the treatment plan. A "cap," as used herein, may refer to a representation of a first portion of a dental appliance that interacts with a tooth or teeth. An example of such first a portion is a part of a polymeric aligner that contacts a tooth or teeth. For instance, a cap may represent contact points of a dental appliance against a tooth. A cap may further represent location(s) of these first portions, size(s) of these first portions, etc. In various implementations, a cap may be associated with a first rigidity.

A "link," as used herein, may refer to a second portion of a dental appliance that connects two or more caps. As noted herein, a links may connect two of the plurality of caps. An example of such second portion is an interproximal region of a polymeric aligner. A link may represent the area between contact points of a dental appliance against two teeth. A link may further represent location(s) of these second portions, size(s) of these second portions, etc. In various implementations, a link may be associated with a second rigidity that is different from the first rigidity. The second rigidity may have a value corresponding to a greater rigidity than the first rigidity. (This may accommodate the fact that interproximal regions of an aligner may be more rigid than the portions of the aligner that interact with specific teeth.)

In some examples methods herein may comprise identifying a relaxed model of a dental appliance using the plurality of caps and the plurality of links. A "relaxed model of a dental appliance," as used herein, may refer to a model of a dental appliance that represents physical properties of the dental appliance when it is manufactured (e.g., through the indirect or direct fabrication techniques described herein). In some examples, the methods herein may comprise identifying a deformed model of the dental appliance to model an approximate use of the dental appliance. A "deformed model of a dental appliance," as used herein, may refer to a model of a dental appliance that represents physical properties of the dental appliance after it has been used in its environment. For instance, a deformed model of an aligner may represent the physical properties of an aligner after the aligner has been inserted into a patient's mouth. A deformed model of an aligner may represent the physical properties of an aligner after the aligner has resided in a patient's mouth for a specified amount of time (e.g., a number of hours, days, etc.). A deformed model of an aligner may represent physical properties of an aligner after its physical properties when manufactured have changed beyond a specified threshold (e.g., after its physical properties when manufactured have sufficiently relaxed due to use in an intraoral or humid environment).

In some examples, the methods herein may comprise identifying relationships (e.g., differences) between the relaxed model of a dental appliance and a deformed model of the dental appliance. The relationships may form the basis of a map between the relaxed model of the dental appliance and a deformed model of the dental appliance. The map may include one or more common attributes, such as common reference points (e.g., common center points) and/or common axes. The map may form the basis of an elastic coordinate system for the dental appliance.

In some examples, methods herein may comprise using the caps and/or links of the relaxed model of the dental appliance and/or the deformed model of the dental appliance to model applying the dental appliance to the initial model of the patient dentition. In some implementations, deviations between the deformed model of the dental appliance and the initial model of the patient dentition may be used to identify application of force(s), torque(s), etc. to move the patient dentition from an initial position (e.g., corresponding to the initial model) toward a target position (e.g., corresponding to the target position). As noted herein, force(s), torque(s), etc. may be calculated by analyzing caps, identifying properties of links, and/or obtaining force(s)/torque(s), etc. using relevant sums of pairs of forces on those caps.

The embodiments disclosed herein may be well suited for combination with one or more commercially available tooth moving components such as attachments and polymeric shell appliances. In some embodiments, the appliance and one or more attachments are configured to move one or more teeth along a tooth movement vector comprising six degrees of freedom, in which three degrees of freedom are rotational and three degrees of freedom are translation.

The present disclosure provides orthodontic appliances and related systems, methods, and devices. Repositioning of teeth may be accomplished with the use of a series of removable elastic positioning appliances such as the Invisalign® system available from Align Technology, Inc., the assignee of the present disclosure. Such appliances may have a thin shell of elastic material that generally conforms to a patient's teeth but is slightly out of alignment with an initial or immediately prior tooth configuration. Placement of the appliance over the teeth applies controlled forces in specific locations to gradually move the teeth into the new configuration. Repetition of this process with successive appliances comprising new configurations eventually moves the teeth through a series of intermediate configurations or alignment patterns to a final desired configuration. Repositioning of teeth may be accomplished through other series of removable orthodontic and/or dental appliances, including polymeric shell appliances.

Although reference is made to an appliance comprising a polymeric shell appliance, the embodiments disclosed herein are well suited for use with many appliances that receive teeth, for example appliances without one or more of polymers or shells. The appliance can be fabricated with one or more of many materials such as metal, glass, reinforced fibers, carbon fiber, composites, reinforced composites, aluminum, biological materials, and combinations thereof for example. The appliance can be shaped in many ways, such as with thermoforming or direct fabrication as described herein, for example. Alternatively or in combination, the appliance can be fabricated with machining such as an appliance fabricated from a block of material with computer numeric control machining. Additionally, though reference is made herein to orthodontic appliances, at least some of the techniques described herein may apply to restorative and/or other dental appliances, including without limitation crowns, veneers, teeth-whitening appliances, teeth-protective appliances, etc.

Appliances

FIG. 1A illustrates an exemplary tooth repositioning appliance or aligner 100 that can be worn by a patient in order to achieve an incremental repositioning of individual teeth 102 in the jaw. The appliance can include a shell (e.g., a continuous polymeric shell or a segmented shell) having teeth-receiving cavities that receive and resiliently reposition the teeth. An appliance or portion(s) thereof may be indirectly fabricated using a physical model of teeth. For example, an appliance (e.g., polymeric appliance) can be formed using a physical model of teeth and a sheet of suitable layers of polymeric material. The physical model (e.g., physical mold) of teeth can be formed through a variety of techniques, including 3D printing. The appliance can be formed by thermoforming the appliance over the physical model. In some embodiments, a physical appliance is directly fabricated, e.g., using additive manufacturing techniques, from a digital model of an appliance. In some embodiments, the physical appliance may be created through a variety of direct formation techniques, such as 3D printing. An appliance can fit over all teeth present in an upper or lower jaw, or less than all of the teeth. The appliance can be designed specifically to accommodate the teeth of the patient (e.g., the topography of the tooth-receiving cavities matches the topography of the patient's teeth), and may be fabricated based on positive or negative models of the patient's teeth generated by impression, scanning, and the like. Alternatively, the appliance can be a generic appliance configured to receive the teeth, but not necessarily shaped to match the topography of the patient's teeth. In some cases, only certain teeth received by an appliance will be repositioned by the appliance while other teeth can provide a base or anchor region for holding the appliance in place as it applies force against the tooth or teeth targeted for repositioning. In some cases, some or most, and even all, of the teeth will be repositioned at some point during treatment. Teeth that are moved can also serve as a base or anchor for holding the appliance as it is worn by the patient.

In some embodiments, no wires or other means will be provided for holding an appliance in place over the teeth. In some cases, however, it may be desirable or necessary to provide individual attachments or other anchoring elements 104 on teeth 102 with corresponding receptacles or apertures 106 in the appliance 100 so that the appliance can apply a selected force on the tooth. Exemplary appliances, including those utilized in the Invisalign® System, are described in numerous patents and patent applications assigned to Align Technology, Inc. including, for example, in U.S. Pat. Nos. 6,450,807, and 5,975,893, as well as on the company's website, which is accessible on the World Wide Web (see, e.g., the url "invisalign.com"). Examples of tooth-mounted attachments suitable for use with orthodontic appliances are also described in patents and patent applications assigned to Align Technology, Inc., including, for example, U.S. Pat. Nos. 6,309,215 and 6,830,450.

Optionally, in cases involving more complex movements or treatment plans, it may be beneficial to utilize auxiliary components (e.g., features, accessories, structures, devices, components, and the like) in conjunction with an orthodontic appliance. Examples of such accessories include but are not limited to elastics, wires, springs, bars, arch expanders, palatal expanders, twin blocks, occlusal blocks, bite ramps, mandibular advancement splints, bite plates, pontics, hooks, brackets, headgear tubes, springs, bumper tubes, palatal bars, frameworks, pin-and-tube apparatuses, buccal shields, buccinator bows, wire shields, lingual flanges and pads, lip pads or bumpers, protrusions, divots, and the like. In some embodiments, the appliances, systems and methods described herein include improved orthodontic appliances with integrally formed features that are shaped to couple to such auxiliary components, or that replace such auxiliary components.

Figure 1B:
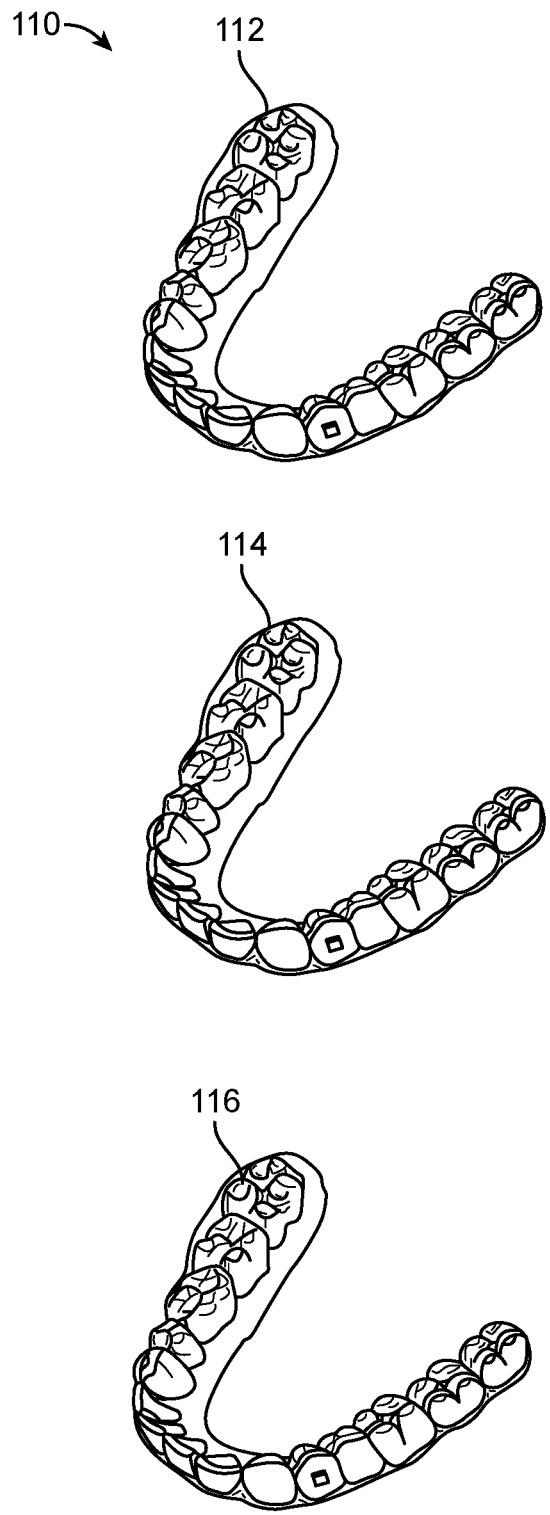
FIG. 1B illustrates a tooth repositioning system, in accordance with one or more embodiments herein.

FIG. 1B illustrates a tooth repositioning system 110 including a plurality of appliances 112, 114, 116. Any of the appliances described herein can be designed and/or provided as part of a set of a plurality of appliances used in a tooth repositioning system. Each appliance may be configured so a tooth-receiving cavity has a geometry corresponding to an intermediate or final tooth arrangement intended for the appliance. The patient's teeth can be progressively repositioned from an initial tooth arrangement towards a target tooth arrangement by placing a series of incremental position adjustment appliances over the patient's teeth. For example, the tooth repositioning system 110 can include a first appliance 112 corresponding to an initial tooth arrangement, one or more intermediate appliances 114 corresponding to one or more intermediate arrangements, and a final appliance 116 corresponding to a target arrangement. A target tooth arrangement can be a planned final tooth arrangement selected for the patient's teeth at the end of all planned orthodontic treatment. Alternatively, a target arrangement can be one of some intermediate arrangements for the patient's teeth during the course of orthodontic treatment, which may include various different treatment scenarios, including, but not limited to, instances where surgery is recommended, where interproximal reduction (IPR) is appropriate, where a progress check is scheduled, where anchor placement is best, where palatal expansion is desirable, where restorative dentistry is involved (e.g., inlays, onlays, crowns, bridges, implants, veneers, and the like), etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

Figure 1C:
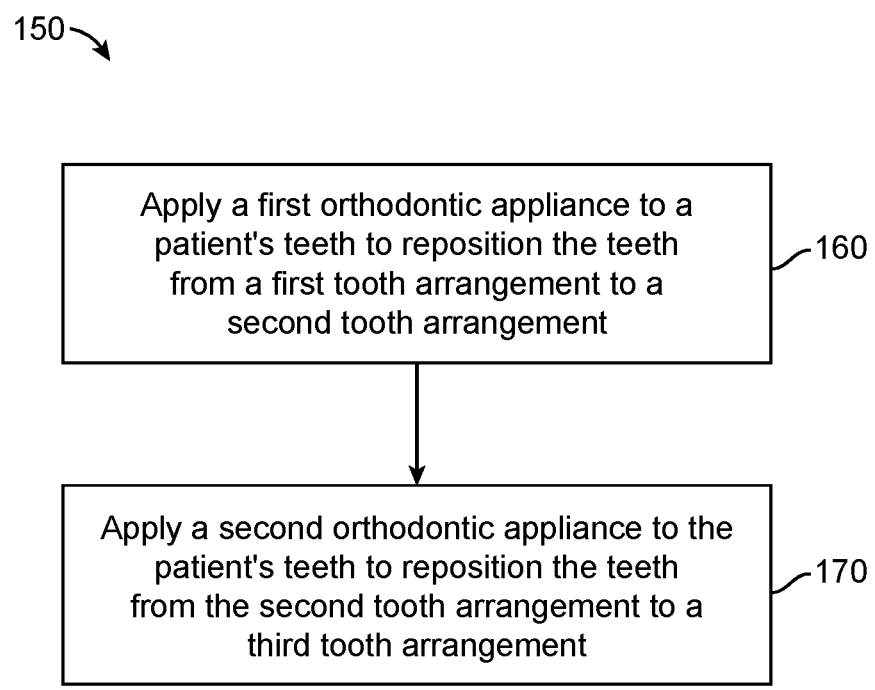
FIG. 1C illustrates a method of orthodontic treatment using a plurality of appliances, in accordance with one or more embodiments herein.

FIG. 1C illustrates a method 150 of orthodontic treatment using a plurality of appliances, in accordance with embodiments. The method 150 can be practiced using any of the appliances or appliance sets described herein. In block 160, a first orthodontic appliance is applied to a patient's teeth in order to reposition the teeth from a first tooth arrangement to a second tooth arrangement. In block 170, a second orthodontic appliance is applied to the patient's teeth in order to reposition the teeth from the second tooth arrangement to a third tooth arrangement. The method 150 can be repeated as necessary using any suitable number and combination of sequential appliances in order to incrementally reposition the patient's teeth from an initial arrangement to a target arrangement. The appliances can be generated all at the same stage or in sets or batches (at the beginning of a stage of the treatment, at an intermediate stage of treatment, etc.), or the appliances can be fabricated one at a time, and the patient can wear each appliance until the pressure of each appliance on the teeth can no longer be felt or until the maximum amount of expressed tooth movement for that given stage has been achieved. A plurality of different appliances (e.g., a set) can be designed and even fabricated prior to the patient wearing any appliance of the plurality. After wearing an appliance for an appropriate period of time, the patient can replace the current appliance with the next appliance in the series until no more appliances remain. The appliances are generally not affixed to the teeth and the patient may place and replace the appliances at any time during the procedure (e.g., patient-removable appliances). The final appliance or several appliances in the series may have a geometry or geometries selected to overcorrect the tooth arrangement. For instance, one or more appliances may have a geometry that would (if fully achieved) move individual teeth beyond the tooth arrangement that has been selected as the "final." Such over-correction may be desirable in order to offset potential relapse after the repositioning method has been terminated (e.g., permit movement of individual teeth back toward their pre-corrected positions). Over-correction may also be beneficial to speed the rate of correction (e.g., an appliance with a geometry that is positioned beyond a desired intermediate or final position may shift the individual teeth toward the position at a greater rate). In such cases, the use of an appliance can be terminated before the teeth reach the positions defined by the appliance. Furthermore, over-correction may be deliberately applied in order to compensate for any inaccuracies or limitations of the appliance.

Appliance Fabrication

The various embodiments of the orthodontic appliances presented herein can be fabricated in a wide variety of ways. In some embodiments, the orthodontic appliances herein (or portions thereof) can be produced using direct fabrication, such as additive manufacturing techniques (also referred to herein as "3D printing) or subtractive manufacturing techniques (e.g., milling). In some embodiments, direct fabrication involves forming an object (e.g., an orthodontic appliance or a portion thereof) without using a physical template (e.g., mold, mask etc.) to define the object geometry. Additive manufacturing techniques can be categorized as follows: (1) vat photopolymerization (e.g., stereolithography), in which an object is constructed layer by layer from a vat of liquid photopolymer resin; (2) material jetting, in which material is jetted onto a build platform using either a continuous or drop on demand (DOD) approach; (3) binder jetting, in which alternating layers of a build material (e.g., a powder-based material) and a binding material (e.g., a liquid binder) are deposited by a print head; (4) fused deposition modeling (FDM), in which material is drawn though a nozzle, heated, and deposited layer by layer; (5) powder bed fusion, including but not limited to direct metal laser sintering (DMLS), electron beam melting (EBM), selective heat sintering (SHS), selective laser melting (SLM), and selective laser sintering (SLS); (6) sheet lamination, including but not limited to laminated object manufacturing (LOM) and ultrasonic additive manufacturing (UAM); and (7) directed energy deposition, including but not limited to laser engineering net shaping, directed light fabrication, direct metal deposition, and 3D laser cladding. For example, stereolithography can be used to directly fabricate one or more of the appliances herein. In some embodiments, stereolithography involves selective polymerization of a photosensitive resin (e.g., a photopolymer) according to a desired cross-sectional shape using light (e.g., ultraviolet light). The object geometry can be built up in a layer-by-layer fashion by sequentially polymerizing a plurality of object cross-sections. As another example, the appliances herein can be directly fabricated using selective laser sintering. In some embodiments, selective laser sintering involves using a laser beam to selectively melt and fuse a layer of powdered material according to a desired cross-sectional shape in order to build up the object geometry. As yet another example, the appliances herein can be directly fabricated by fused deposition modeling. In some embodiments, fused deposition modeling involves melting and selectively depositing a thin filament of thermoplastic polymer in a layer-by-layer manner in order to form an object. In yet another example, material jetting can be used to directly fabricate the appliances herein. In some embodiments, material jetting involves jetting or extruding one or more materials onto a build surface in order to form successive layers of the object geometry.

In some embodiments, the direct fabrication methods provided herein build up the object geometry in a layer-by-layer fashion, with successive layers being formed in discrete build steps. Alternatively or in combination, direct fabrication methods that allow for continuous build-up of an object's geometry can be used, referred to herein as "continuous direct fabrication." Various types of continuous direct fabrication methods can be used. As an example, in some embodiments, the appliances herein are fabricated using "continuous liquid interphase printing," in which an object is continuously built up from a reservoir of photopolymerizable resin by forming a gradient of partially cured resin between the building surface of the object and a polymerization-inhibited "dead zone." In some embodiments, a semi-permeable membrane is used to control transport of a photopolymerization inhibitor (e.g., oxygen) into the dead zone in order to form the polymerization gradient. Continuous liquid interphase printing can achieve fabrication speeds about 25 times to about 100 times faster than other direct fabrication methods, and speeds about 1000 times faster can be achieved with the incorporation of cooling systems. Continuous liquid interphase printing is described in U.S. Patent Publication Nos. 2015/0097315, 2015/0097316, and 2015/0102532, (corresponding to U.S. Pat. Nos. corresponding to U.S. Pat. Nos. 9,205,601, 9,216, 546, and 9,211,678) the disclosures of each of which are incorporated herein by reference in their entirety.

As another example, a continuous direct fabrication method can achieve continuous build-up of an object geometry by continuous movement of the build platform (e.g., along the vertical or Z-direction) during the irradiation phase, such that the hardening depth of the irradiated photopolymer is controlled by the movement speed. Accordingly, continuous polymerization of material on the build surface can be achieved. Such methods are described in U.S. Pat. No. 7,892,474, the disclosure of which is incorporated herein by reference in its entirety.

In another example, a continuous direct fabrication method can involve extruding a composite material composed of a curable liquid material surrounding a solid strand. The composite material can be extruded along a continuous 3D path in order to form the object. Such methods are described in U.S. Patent Publication No. 2014/0061974, corresponding to U.S. Pat. No. 9,511,543, the disclosures of which are incorporated herein by reference in its entirety.

In yet another example, a continuous direct fabrication method utilizes a "heliolithography" approach in which the liquid photopolymer is cured with focused radiation while the build platform is continuously rotated and raised. Accordingly, the object geometry can be continuously built up along a spiral build path. Such methods are described in U.S. Patent Publication No. 2014/0265034, corresponding to U.S. Pat. No. 9,321,215, the disclosures of which are incorporated herein by reference in its entirety.

The direct fabrication approaches provided herein are compatible with a wide variety of materials, including but not limited to one or more of the following: polymer matrix reinforced with ceramic or metallic polymers, a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, a polytrimethylene terephthalate, a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, a thermoplastic polyamide elastomer, or combinations thereof. The materials used for direct fabrication can be provided in an uncured form (e.g., as a liquid, resin, powder, etc.) and can be cured (e.g., by photopolymerization, light curing, gas curing, laser curing, crosslinking, etc.) in order to form an orthodontic appliance or a portion thereof. The properties of the material before curing may differ from the properties of the material after curing. Once cured, the materials herein can exhibit sufficient strength, stiffness, durability, biocompatibility, etc. for use in an orthodontic appliance. The post-curing properties of the materials used can be selected according to the desired properties for the corresponding portions of the appliance.

In some embodiments, relatively rigid portions of the orthodontic appliance can be formed via direct fabrication using one or more of the following materials: a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, and/or a polytrimethylene terephthalate.

In some embodiments, relatively elastic portions of the orthodontic appliance can be formed via direct fabrication using one or more of the following materials: a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, and/or a thermoplastic polyamide elastomer.

Optionally, the direct fabrication methods described herein allow for fabrication of an appliance including multiple materials, referred to herein as "multi-material direct fabrication." In some embodiments, a multi-material direct fabrication method involves concurrently forming an object from multiple materials in a single manufacturing step using the same fabrication machine and method. For instance, a multi-tip extrusion apparatus can be used to selectively dispense multiple types of materials (e.g., resins, liquids, solids, or combinations thereof) from distinct material supply sources in order to fabricate an object from a plurality of different materials. Such methods are described in U.S. Pat. No. 6,749,414, the disclosure of which is incorporated herein by reference in its entirety. Alternatively or in combination, a multi-material direct fabrication method can involve forming an object from multiple materials in a plurality of sequential manufacturing steps. For instance, a first portion of the object can be formed from a first material in accordance with any of the direct fabrication methods herein, then a second portion of the object can be formed from a second material in accordance with methods herein, and so on, until the entirety of the object has been formed. The relative arrangement of the first and second portions can be varied as desired, e.g., the first portion can be partially or wholly encapsulated by the second portion of the object. The sequential manufacturing steps can be performed using the same fabrication machine or different fabrication machines, and can be performed using the same fabrication method or different fabrication methods. For example, a sequential multi-manufacturing procedure can involve forming a first portion of the object using stereolithography and a second portion of the object using fused deposition modeling.

Direct fabrication can provide various advantages compared to other manufacturing approaches. For instance, in contrast to indirect fabrication, direct fabrication permits production of an orthodontic appliance without utilizing any molds or templates for shaping the appliance, thus reducing the number of manufacturing steps involved and improving the resolution and accuracy of the final appliance geometry. Additionally, direct fabrication permits precise control over the 3D geometry of the appliance, such as the appliance thickness. Complex structures and/or auxiliary components can be formed integrally as a single piece with the appliance shell in a single manufacturing step, rather than being added to the shell in a separate manufacturing step. In some embodiments, direct fabrication is used to produce appliance geometries that would be difficult to create using alternative manufacturing techniques, such as appliances with very small or fine features, complex geometric shapes, undercuts, interproximal structures, shells with variable thicknesses, and/or internal structures (e.g., for improving strength with reduced weight and material usage). For example, in some embodiments, the direct fabrication approaches herein permit fabrication of an orthodontic appliance with feature sizes of less than or equal to about 5 µm, or within a range from about 5 µm to about 50 µm, or within a range from about 20 µm to about 50 µm.

In some embodiments, the direct fabrication methods described herein implement process controls for various machine parameters of a direct fabrication system or device in order to ensure that the resultant appliances are fabricated with a high degree of precision. Such precision can be beneficial for ensuring accurate delivery of a desired force system to the teeth in order to effectively elicit tooth movements. Process controls can be implemented to account for process variability arising from multiple sources, such as the material properties, machine parameters, environmental variables, and/or post-processing parameters.

Material properties may vary depending on the properties of raw materials, purity of raw materials, and/or process variables during mixing of the raw materials. In many embodiments, resins or other materials for direct fabrication should be manufactured with tight process control to ensure little variability in photo-characteristics, material properties (e.g., viscosity, surface tension), physical properties (e.g., modulus, strength, elongation) and/or thermal properties (e.g., glass transition temperature, heat deflection temperature). Process control for a material manufacturing process can be achieved with screening of raw materials for physical properties and/or control of temperature, humidity, and/or other process parameters during the mixing process. By implementing process controls for the material manufacturing procedure, reduced variability of process parameters and more uniform material properties for each batch of material can be achieved. Residual variability in material properties can be compensated with process control on the machine, as discussed further herein.

Machine parameters can include curing parameters. For digital light processing (DLP)-based curing systems, curing parameters can include power, curing time, and/or grayscale of the full image. For laser-based curing systems, curing parameters can include power, speed, beam size, beam shape and/or power distribution of the beam. For printing systems, curing parameters can include material drop size, viscosity, and/or curing power. These machine parameters can be monitored and adjusted on a regular basis (e.g., some parameters at every 1-x layers and some parameters after each build) as part of the process control on the fabrication machine. Process control can be achieved by including a sensor on the machine that measures power and other beam parameters every layer or every few seconds and automatically adjusts them with a feedback loop. For DLP machines, gray scale can be measured and calibrated before, during, and/or at the end of each build, and/or at predetermined time intervals (e.g., every $n^{th}$ build, once per hour, once per day, once per week, etc.), depending on the stability of the system. In addition, material properties and/or photo-characteristics can be provided to the fabrication machine, and a machine process control module can use these parameters to adjust machine parameters (e.g., power, time, gray scale, etc.) to compensate for variability in material properties. By implementing process controls for the fabrication machine, reduced variability in appliance accuracy and residual stress can be achieved.

In many embodiments, environmental variables (e.g., temperature, humidity, Sunlight or exposure to other energy/curing source) are maintained in a tight range to reduce variable in appliance thickness and/or other properties. Optionally, machine parameters can be adjusted to compensate for environmental variables.

In many embodiments, post-processing of appliances includes cleaning, post-curing, and/or support removal processes. Relevant post-processing parameters can include purity of cleaning agent, cleaning pressure and/or temperature, cleaning time, post-curing energy and/or time, and/or consistency of support removal process. These parameters can be measured and adjusted as part of a process control scheme. In addition, appliance physical properties can be varied by modifying the post-processing parameters. Adjusting post-processing machine parameters can provide another way to compensate for variability in material properties and/or machine properties.

Although various embodiments herein are described with respect to direct fabrication techniques, it shall be appreciated that other techniques can also be used, such as indirect fabrication techniques. In some embodiments, the appliances herein (or portions thereof) can be produced using indirect fabrication techniques, such as by thermoforming over a positive or negative mold. Indirect fabrication of an orthodontic appliance can involve one or more of the following steps: producing a positive or negative mold of the patient's dentition in a target arrangement (e.g., by additive manufacturing, milling, etc.), thermoforming one or more sheets of material over the mold in order to generate an appliance shell, forming one or more structures in the shell (e.g., by cutting, etching, etc.), and/or coupling one or more components to the shell (e.g., by extrusion, additive manufacturing, spraying, thermoforming, adhesives, bonding, fasteners, etc.). Optionally, one or more auxiliary appliance components as described herein (e.g., elastics, wires, springs, bars, arch expanders, palatal expanders, twin blocks, occlusal blocks, bite ramps, mandibular advancement splints, bite plates, pontics, hooks, brackets, headgear tubes, bumper tubes, palatal bars, frameworks, pin-and-tube apparatuses, buccal shields, buccinator bows, wire shields, lingual flanges and pads, lip pads or bumpers, protrusions, divots, etc.) are formed separately from and coupled to the appliance shell (e.g., via adhesives, bonding, fasteners, mounting features, etc.) after the shell has been fabricated.

In some embodiments, the orthodontic appliances herein can be fabricated using a combination of direct and indirect fabrication techniques, such that different portions of an appliance can be fabricated using different fabrication techniques and assembled in order to form the final appliance.

For example, an appliance shell can be formed by indirect fabrication (e.g., thermoforming), and one or more structures or components as described herein (e.g., auxiliary components, power arms, etc.) can be added to the shell by direct fabrication (e.g., printing onto the shell).

Methods of Design

Figure 2:
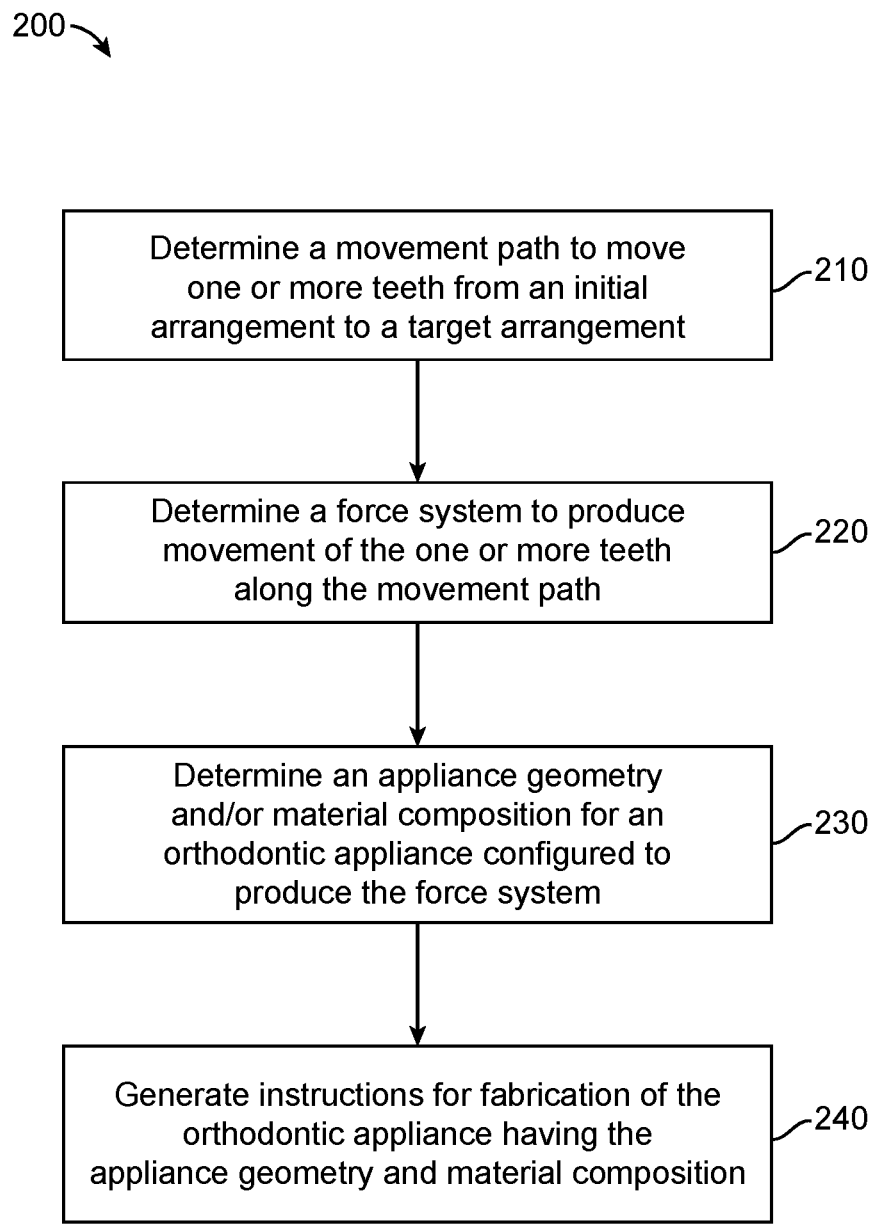
FIG. 2 illustrates a method for designing an orthodontic appliance, in accordance with one or more aspects of the methods disclosed herein.

FIG. 2 illustrates a method 200 for designing an orthodontic appliance to be fabricated, in accordance with embodiments. The method 200 can be applied to any embodiment of the orthodontic appliances described herein. Some or all of the operations of the method 200 can be performed by any suitable data processing system or device, e.g., one or more processors configured with suitable instructions.

In block 210, a movement path to move one or more teeth from an initial arrangement to a target arrangement is determined. The initial arrangement can be determined from a mold or a scan of the patient's teeth or mouth tissue, e.g., using wax bites, direct contact scanning, x-ray imaging, tomographic imaging, sonographic imaging, and other techniques for obtaining information about the position and structure of the teeth, jaws, gums and other orthodontically relevant tissue. From the obtained data, a digital data set can be derived that represents the initial (e.g., pretreatment) arrangement of the patient's teeth and other tissues. Optionally, the initial digital data set is processed to segment the tissue constituents from each other. For example, data structures that digitally represent individual tooth crowns can be produced. Advantageously, digital models of entire teeth can be produced, including measured or extrapolated hidden surfaces and root structures, as well as surrounding bone and soft tissue.

The target arrangement of the teeth (e.g., a desired and intended end result of orthodontic treatment) can be received from a clinician in the form of a prescription, can be calculated from basic orthodontic principles, and/or can be extrapolated computationally from a clinical prescription. With a specification of the desired final positions of the teeth and a digital representation of the teeth themselves, the final position and surface geometry of each tooth can be specified to form a complete model of the tooth arrangement at the desired end of treatment.

Having both an initial position and a target position for each tooth, a movement path can be defined for the motion of each tooth. In some embodiments, the movement paths are configured to move the teeth in the quickest fashion with the least amount of round-tripping to bring the teeth from their initial positions to their desired target positions. The tooth paths can optionally be segmented, and the segments can be calculated so that each tooth's motion within a segment stays within threshold limits of linear and rotational translation. In this way, the end points of each path segment can constitute a clinically viable repositioning, and the aggregate of segment end points can constitute a clinically viable sequence of tooth positions, so that moving from one point to the next in the sequence does not result in a collision of teeth.

In block 220, a force system to produce movement of the one or more teeth along the movement path is determined. In some embodiments, the torque system may be determined. A moment system may be determined. A force system can include one or more forces and/or one or more torques. Different force systems can result in different types of tooth movement, such as tipping, translation, rotation, extrusion, intrusion, root movement, etc. Biomechanical principles, modeling techniques, force calculation/measurement techniques, and the like, including knowledge and approaches commonly used in orthodontia, may be used to determine the appropriate force system to be applied to the tooth to accomplish the tooth movement. In determining the force system to be applied, sources may be considered including literature, force systems determined by experimentation or virtual modeling, computer-based modeling, clinical experience, minimization of unwanted forces, etc.

Determination of the force system can be performed in a variety of ways. For example, in some embodiments, the force system is determined on a patient-by-patient basis, e.g., using patient-specific data. Alternatively or in combination, the force system can be determined based on a generalized model of tooth movement (e.g., based on experimentation, modeling, clinical data, etc.), such that patient-specific data is not necessarily used. In some embodiments, determination of a force system involves calculating specific force values to be applied to one or more teeth to produce a particular movement. Alternatively, determination of a force system can be performed at a high level without calculating specific force values for the teeth. For instance, block 220 can involve determining a particular type of force to be applied (e.g., extrusive force, intrusive force, translational force, rotational force, tipping force, torqueing force, etc.) without calculating the specific magnitude and/or direction of the force.

In block 230, an appliance geometry and/or material composition for an orthodontic appliance configured to produce the force system is determined. The appliance can be any embodiment of the appliances discussed herein, such as an appliance having variable localized properties, integrally formed components, and/or power arms.

For example, in some embodiments, the appliance comprises a heterogeneous thickness, a heterogeneous stiffness, or a heterogeneous material composition. In some embodiments, the appliance comprises two or more of a heterogeneous thickness, a heterogeneous stiffness, or a heterogeneous material composition. In some embodiments, the appliance comprises a heterogeneous thickness, a heterogeneous stiffness, and a heterogeneous material composition. The heterogeneous thickness, stiffness, and/or material composition can be configured to produce the force system for moving the teeth, e.g., by preferentially applying forces at certain locations on the teeth. For example, an appliance with heterogeneous thickness can include thicker portions that apply more force on the teeth than thinner portions. As another example, an appliance with heterogeneous stiffness can include stiffer portions that apply more force on the teeth than more elastic portions. Variations in stiffness can be achieved by varying the appliance thickness, material composition, and/or degree of photopolymerization, as described herein.

In some embodiments, determining the appliance geometry and/or material composition comprises determining the geometry and/or material composition of one or more integrally formed components to be directly fabricated with an appliance shell. The integrally formed component can be any of the embodiments described herein. The geometry and/or material composition of the integrally formed component(s) can be selected to facilitate application of the force system onto the patient's teeth. The material composition of the integrally formed component can be the same as or different from the material composition of the shell.

The block 230 can involve analyzing the desired force system in order to determine an appliance geometry and material composition that would produce the force system. In some embodiments, the analysis involves determining appliance properties (e.g., stiffness) at one or more locations that would produce a desired force at the one or more locations. The analysis can then involve determining an appliance geometry and material composition at the one or more locations to achieve the specified properties. Determination of the appliance geometry and material composition can be performed using a treatment or force application simulation environment. A simulation environment can include, e.g., computer modeling systems, biomechanical systems or apparatus, and the like. Optionally, digital models of the appliance and/or teeth can be produced, such as finite element models. The finite element models can be created using computer program application software available from a variety of vendors. For creating solid geometry models, computer aided engineering (CAE) or computer aided design (CAD) programs can be used, such as the AutoCAD® software products available from Autodesk, Inc., of San Rafael, Calif. For creating finite element models and analyzing them, program products from a number of vendors can be used, including finite element analysis packages from ANSYS, Inc., of Canonsburg, Pa., and SIMIULIA (Abaqus) software products from Dassault Systèmes of Waltham, Mass.

Optionally, one or more appliance geometries and material compositions can be selected for testing or force modeling. As noted above, a desired tooth movement, as well as a force system required or desired for eliciting the desired tooth movement, can be identified. Using the simulation environment, a candidate appliance geometry and composition can be analyzed or modeled for determination of an actual force system resulting from use of the candidate appliance. One or more modifications can optionally be made to a candidate appliance, and force modeling can be further analyzed as described, e.g., in order to iteratively determine an appliance design that produces the desired force system.

Optionally, block 230 can further involve determining the geometry of one or more auxiliary components to be used in combination with the orthodontic appliance in order to exert the force system on the one or more teeth. Such auxiliaries can include one or more of tooth-mounted attachments, elastics, wires, springs, bite blocks, arch expanders, wire-and-bracket appliances, shell appliances, headgear, or any other orthodontic device or system that can be used in conjunction with the orthodontic appliances herein. The use of such auxiliary components may be advantageous in situations where it is difficult for the appliance alone to produce the force system. Additionally, auxiliary components can be added to the orthodontic appliance in order to provide other desired functionalities besides producing the force system, such as mandibular advancement splints to treat sleep apnea, pontics to improve aesthetic appearance, and so on. In some embodiments, the auxiliary components are fabricated and provided separately from the orthodontic appliance. Alternatively, the geometry of the orthodontic appliance can be modified to include one or more auxiliary components as integrally formed components.

In block 240, instructions for fabrication of the orthodontic appliance having the appliance geometry and material composition are generated. The instructions can be configured to control a fabrication system or device in order to produce the orthodontic appliance with the specified appliance geometry and material composition. In some embodiments, the instructions are configured for manufacturing the orthodontic appliance using direct fabrication (e.g., stereolithography, selective laser sintering, fused deposition modeling, 3D printing, continuous direct fabrication, multi-material direct fabrication, etc.). In alternative embodiments, the instructions can be configured for indirect fabrication of the appliance, e.g., by thermoforming.

Although the above blocks show a method 200 of designing an orthodontic appliance in accordance with some embodiments, a person of ordinary skill in the art will recognize some variations based on the teaching described herein. Some of the blocks may comprise sub-blocks. Some of the blocks may be repeated as often as desired. One or more blocks of the method 200 may be performed with any suitable fabrication system or device, such as the embodiments described herein. Some of the blocks may be optional, and the order of the blocks can be varied as desired. For instance, in some embodiments, block 220 is optional, such that block 230 involves determining the appliance geometry and/or material composition based directly on the tooth movement path rather than based on the force system.

Treatment Planning

Figure 3:
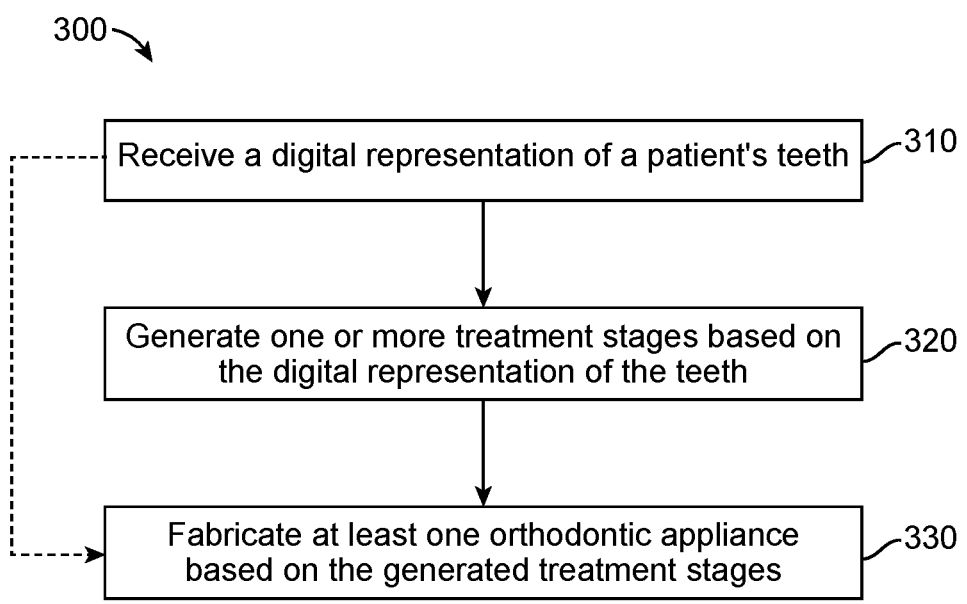
FIG. 3 illustrates a method for planning an orthodontic treatment, in accordance with one or more embodiments herein.

FIG. 3 illustrates a method 300 for digitally planning an orthodontic treatment and/or design or fabrication of an appliance, in accordance with embodiments. The method 300 can be applied to any of the treatment procedures described herein and can be performed by any suitable data processing system.

In block 310, a digital representation of a patient's teeth is received. The digital representation can include surface topography data for the patient's intraoral cavity (including teeth, gingival tissues, etc.). The surface topography data can be generated by directly scanning the intraoral cavity, a physical model (positive or negative) of the intraoral cavity, or an impression of the intraoral cavity, using a suitable scanning device (e.g., a handheld scanner, desktop scanner, etc.).

In block 320, one or more treatment stages are generated based on the digital representation of the teeth. The treatment stages can be incremental repositioning stages of an orthodontic treatment procedure designed to move one or more of the patient's teeth from an initial tooth arrangement to a target arrangement. For example, the treatment stages can be generated by determining the initial tooth arrangement indicated by the digital representation, determining a target tooth arrangement, and determining movement paths of one or more teeth in the initial arrangement necessary to achieve the target tooth arrangement. The movement path can be optimized based on minimizing the total distance moved, preventing collisions between teeth, avoiding tooth movements that are more difficult to achieve, or any other suitable criteria.

In block 330, at least one orthodontic appliance is fabricated based on the generated treatment stages. For example, a set of appliances can be fabricated, each shaped according to a tooth arrangement specified by one of the treatment stages, such that the appliances can be sequentially worn by the patient to incrementally reposition the teeth from the initial arrangement to the target arrangement. Each aligner may translate each tooth at most about 0.25 mm over a period from one to two weeks. Each aligner may rotate each tooth at most about 2 degrees over a period of time from 1 to 2 weeks. The appliance set may include one or more of the orthodontic appliances described herein. The fabrication of the appliance may involve creating a digital model of the appliance to be used as input to a computer-controlled fabrication system. The appliance can be formed using direct fabrication methods, indirect fabrication methods, or combinations thereof, as desired.

In some instances, staging of various arrangements or treatment stages may not be necessary for design and/or fabrication of an appliance. As illustrated by the dashed line in FIG. 3, design and/or fabrication of an orthodontic appliance, and perhaps a particular orthodontic treatment, may include use of a representation of the patient's teeth (e.g., receive a digital representation of the patient's teeth 310), followed by design and/or fabrication of an orthodontic appliance based on a representation of the patient's teeth in the arrangement represented by the received representation.

Optionally, some or all of the blocks of the method 300 are performed locally at the site where the patient is being treated and during a single patient visit, referred to herein as "chair side manufacturing." Chair side manufacturing can involve, for example, scanning the patient's teeth, automatically generating a treatment plan with treatment stages, and immediately fabricating one or more orthodontic appliance(s) to treat the patient using a chair side direct fabrication machine, all at the treating professional's office during a single appointment. In embodiments where a series of appliances are used to treat the patient, the first appliance may be produced chair side for immediate delivery to the patient, with the remaining appliances produced separately (e.g., off site at a lab or central manufacturing facility) and delivered at a later time (e.g., at a follow up appointment, mailed to the patient). Alternatively, the methods herein can accommodate production and immediate delivery of the entire series of appliances on site during a single visit. Chair side manufacturing can thus improve the convenience and speed of the treatment procedure by allowing the patient to immediately begin treatment at the practitioner's office, rather than having to wait for fabrication and delivery of the appliances at a later date. Additionally, chair side manufacturing can provide improved flexibility and efficiency of orthodontic treatment. For instance, in some embodiments, the patient is re-scanned at each appointment to determine the actual positions of the teeth, and the treatment plan is updated accordingly. Subsequently, new appliances can be immediately produced and delivered chair side to accommodate any changes to or deviations from the treatment plan.

Appliance Modeling

In some embodiments, the present disclosure provides systems and methods which improve a computational time to model a stage or a series of stages in a treatment plan. In some cases, the method may be used to model a treatment plan. The method may reduce the number of optimized parameters over models based on finite element analysis. Methods and systems may make approximations in order to reduce computational cost. In some embodiments, the present disclosure provides for designing an orthodontic appliance to be fabricated.

Figure 4:
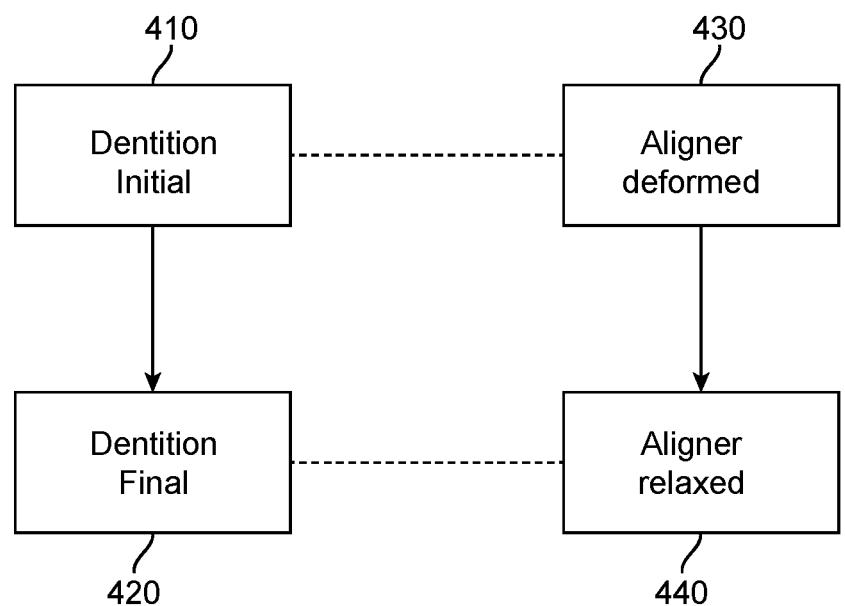
FIG. 4 shows a relationship between the initial and final representation of the patient dentition and the relaxed and deformed model of the aligner, in accordance with one or more embodiments herein.

FIG. 4 shows a relationship between the initial and final representation of the patient dentition and the relaxed and deformed model of the aligner, in accordance with some embodiments. The initial 410 and final 420 representation may relate to the position of the patient teeth, while the deformed 430 and relaxed models 440 may relate to the configuration of the aligner. Before a stage in a treatment plan, the patient dentition may be in an initial configuration, and the aligner may be significantly deformed when is inserted in the patient mouth. Over time, the aligner may relax as the teeth move in response to the force on the teeth generated by the aligner. After a stage in the treatment plan, the aligner may comprise a relaxed or a more relaxed geometry than at the beginning of the stage in the treatment plan. In order to produce an effective aligner, it may be beneficial to know the magnitude and direction of forces and moments to apply to the patient's teeth.

Figure 5A:
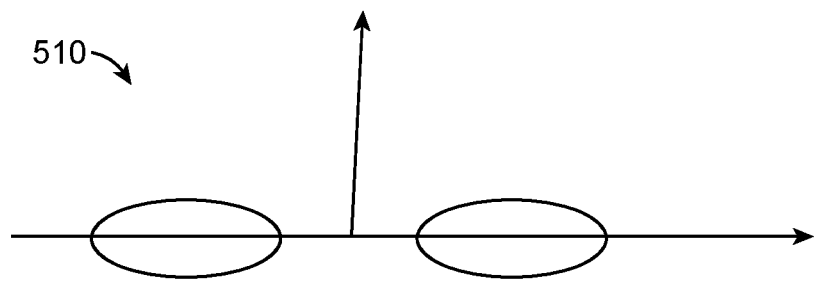
FIG. 5A shows a simplified schematic rendering of two sets two caps each joined by a link, in accordance with one or more embodiments herein.
Figure 5A:
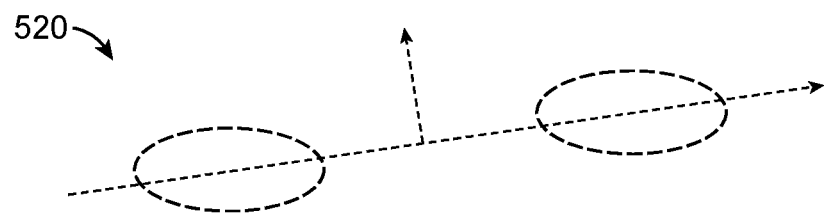

FIG. 5A shows a simple schematic rendering of two sets two caps each joined by a link. In some embodiments, the caps may be an abstraction of a tooth receiving cavity, representing physical properties, such as their position, orientation, shape, etc. in two or three dimensional space. In some embodiments, the cap may comprise a reduced dimensional surface representing the shape of an individual tooth. In some cases, the shape of a tooth may be approximated by a cylinder or an elliptic cylinder. The cap may be a rigid body that may translate and rotate within the model. The cap may represent a contact point on a tooth of the dentition. In some cases, the shape of the tooth may be approximated from three-dimensional rendering of a tooth from a finite element analysis model. The shape of the tooth may be approximated by a finite element analysis model with a minimal or reduced discretization of the surface. For example, the cap may be approximated by a lower fidelity finite element model than is used to manufacture an aligner. The fidelity of the model may be reduced to decrease computational cost of a model of the force/moment system of the patient dentition. In some cases, the cap may approximate the same contour or shape of the tooth. In some cases, deformations in the shape of the cap may not be considered in the deformed model. In some cases, only small deformations in the shape of the cap may be considered.

The link may be an abstraction that represents the aligner material that makes up and connects two tooth receiving cavities, represented by caps. A link may represent a connection between two of the plurality of caps. In some cases, the link may connect two adjacent caps. In some cases, the link may connect to caps which are not adjacent. In some cases, the link may be approximated by line segment connecting the caps. The link to be used in the relaxed and deformed model may comprise a Hookian stiffness parameter. The Hookian stiffness parameter may represented by a constant with distance. In some cases, the stiffness parameter may be represented by a higher order polynomial, for example, a quadratic, a third order polynomial, or higher. In some cases, the stiffness parameter may be represented by a matrix comprising a different stiffness parameter in each spatial dimension. In some cases, the link may be approximated by a finite element analysis model with a minimal or reduced discretization of the surface. For example, the link may be approximated by a lower fidelity finite element model than is used to manufacture an aligner. The fidelity of the model may be reduced to decrease computational cost of a model of the force/moment system of the patient dentition.

In some embodiments, a relaxed model may be generated. In some examples the method may comprise generating a relaxed model of a dental appliance from the plurality of caps and the plurality of links. The relaxed model may represent an arrangement of caps and links which relates to the representation of the patient dentition after a stage of the treatment plan or of aligner. The tooth receiving cavities may be arranged to impart a tooth moving force on one or more teeth of the patient. Before the appliance is attached to a patient jaw, the appliance may be in a configuration that relates to the relaxed model of the aligner. Before application of the appliance on the patient teeth, the appliance may be in a relaxed and original manufactured shape. Before the application of the appliance on the patient teeth, the positions of the caps may be in relaxed positions.

In some embodiments, a deformed model may be generated. In some examples the method may comprise generating a deformed model of a dental appliance from the plurality of caps and plurality of links. The deformed model may represent an arrangement of caps and links which relates to the representation of the patient dentition before a stage of the treatment plan. After the appliance is attached to a patient's arch and before progression of tooth movement, the appliance may be in a configuration that relates to the deformed model of the aligner. After application of the appliance on the patient teeth, the appliance may be in a deformed shape. The degree to which the appliance may be deformed may change as a function of time and as the teeth move. In some cases, the position of the deformed caps may be the same as the teeth positions, such as if the fit is perfect. In some cases, the position of the deformed caps may also be different. Such effect may be limited by the stiffness and/or compliance of the appliance material. After the application of the appliance on the patient teeth, the positions of the caps may be in the deformed position.

FIG. 5A shows an example of relaxed 510 and deformed 520 cap positions in a model of dentition comprising two teeth. In some embodiments, an elastic coordinate system may be defined. As shown in the illustrated embodiment, the elastic coordinate of for each of the relaxed and deformed positions is indicated by the arrows. In some embodiments, a relaxed model and a deformed model of the aligner may be defined.

In some embodiments, a coordinate system based on the center of the pair of caps may be defined. If the pair is moved together, the position of each tooth relative to the center coordinate system may be unchanged. Such a coordinate system may be called the elastic coordinate C. The elastic coordinate origin may be at the center of two caps: $C=(C_1+C_2)/2$, where $C_1$, $C_2$ may be the center of each cap of each of the two teeth. In some cases, Y may be the distance (mesial/distal) direction of two teeth: $y=(C_2-C_1)$, and X may be the buccal-lingual direction of two teeth and related to Y by $x=y\times(\hat{z}_1+\hat{z}_2)/2$. Finally, Z may be the extrusion direction of two teeth and $z=x\times y$.

Figure 5B:
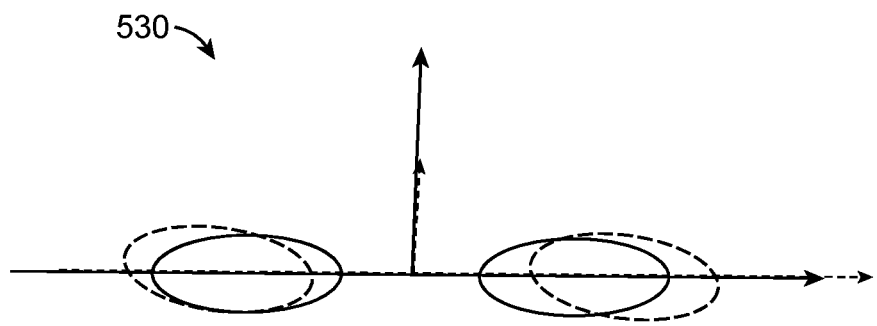
FIG. 5B shows a pair of exemplary caps whose relaxed and deformed coordinates have been mapped together, in accordance with one or more embodiments herein.

FIG. 5B shows a pair of exemplary caps 530 whose relaxed and deformed coordinates have been mapped together. In some cases, the method may comprise mapping the relaxed coordinate to the deformed coordinate. In some cases, the relaxed coordinate may have the same center as the deformed coordinate. After transformation, the relaxed coordinate may have the same axes as the deformed coordinate. Mapping the relaxed coordinate onto the deformed coordinate may assure that there is no total displacement or rotation force on the arch.

In some embodiments, a plurality of transformational parameters may be determined. The transformational parameters may comprise a plurality of moments and/or a plurality of forces associated with the caps. In some embodiments, the force and moment between any two neighboring caps may be nonlinearly related to the translational and rotational movement. The nonlinear parts may include but are not limited to the cross products of the rotation vector and the distance vector between two teeth or the teeth direction. A force system can include one or more forces and/or one or more torques. Different force systems can result in different types of tooth movement, such as tipping, translation, rotation, extrusion, intrusion, root movement, etc. Determination of the force system can be performed in a variety of ways. For example, in some embodiments, the force system is determined on a patient-by-patient basis, e.g., using patient-specific data.

In some embodiments, the forces and/or moments may be determined for each pair of teeth connected by a link. The forces for each pair may then be summed in order to generate a model of the whole jaw or whole arch system. A reduced model of the forces and/or moments on each tooth may comprise forming pairs of neighboring caps. Each two neighboring caps may be connected by their links. The moment may be obtained from the sum of all the pairs. The total force and/or moment may be defined as sum of forces and/or moments of all pairs. Without being limited by theory, if the appliance as a whole is moved, there should be no force on the pair. If the appliance as a whole is moved either by rotating or translating the appliance as a whole, there should be no force on the pair.

As shown in FIG. 5B, after mapping the relaxed and deformed coordinate onto one another, each tooth may be individually rotated or displaced from relaxed to deformed. The difference between the relaxed and deformed position of the first cap may be defined as $(\theta_1, T_1)$, where $\theta_1$ may be the rotation angle for each axis for the first cap from the deformed to relaxed orientation and where $T_1$ may be the translation of the first cap from the deformed to relaxed position. The rotation matrix or quaternion Q may then be defined as follows:

$$(\theta_1, T_1) \sim (Q(\theta_1), T_1) = (Q(\theta_{1R})Q(\theta_{1D})^{-1}, T_{1R} - T_{1D}).$$

Similarly for the second cap, the difference may be defined as $(\theta_2, T_2)$ where $\theta_2$ may be the rotation angle for each axis for the first cap from the deformed to relaxed orientation and where $T_2$ may be the translation of the first cap from the deformed to relaxed position. The convention above may move the negative sign in Hooke's law into the difference.

In the illustrated embodiment, only a translation in the medial-distal direction, Ty, survives, which may be represented as follows:

$$Tx=0, Tz=0, T_{1y}=-T_{2y}.$$

Therefore, the force in the medial-distal direction may be represented as:

$$F_{1y}=\alpha(T_{1y}-T_{2y})=2\alpha T_{1y}=-F_{2y}.$$

In the illustrated embodiment, there is no net moment from translation (i.e. each tooth moves in an equal and opposite direction). In the example, the number of translation coordinates may be reduced as $T_x$ and $T_z$ are replaced by two teeth with equal rotation plus a small $T_y$.

In some examples, the method may comprise determining a plurality of moments, wherein the plurality of moments transform the relaxed model to the deformed model and wherein the moments are configured to direct the patient dentition from the initial model to the target model. In an example, one may consider a case where there may be only $\theta_1$, moment on $T_1$ and $T_2$. In such as case, the rotational moment may be defined by the following:

$$M_{11}^L=\beta\theta_1, M_{21}^L=-\beta\theta_1,$$

where β is 3×3 matrix relating the magnitude of the rotation, which may be mainly diagonal (3 Params). Alternatively, in an example case where there may be only $\theta_2$, the moment on $T_1$ and $T_2$ may be defined as $M_{22}^L=\beta\theta_2$, $M_{12}^L=-\beta\theta_2$. In cases where there may be non-zero $\theta_1$, $\theta_2$, the moment may be:

$$M_1^L=\beta(\theta_1-\theta_2), M_2^L=\beta(\theta_2-\theta_1).$$

From the moment, the linear part of the rotation force may be defined. For a case with both $\theta_1$, $\theta_2$, the force may be:

$$F_1^L=(\theta_1-\theta_2), F_2^L=\psi(\theta_2-\theta_1),$$

where ψ is a 3×3 stiffness matrix. The largest components to the stiffness matrix may be xy and yx. In some embodiments the force pair may be balanced. In some cases an extra moment may be defined to balance the force pair, which may be defined as:

$$M_1'^L = M_2'^L = \psi(\theta_1 - \theta_2) \times \frac{y_{12}}{2}.$$

When $\theta_1 = \theta_2$, all linear parts may be zero. Translations in X and Z may require a nonzero linear term.

In a first example, the cross product of the force in the medial-distal direction may be quadratic. In some embodiments, the rotation force may be quadratic. In an example, the force may be $F = \gamma(\theta \times y)$, where y is distance vector of two teeth. The direction of F may be quadratic of two vector ($\theta$, y), its magnitude may linear in R, and $\gamma$ may be a 3×3 stiffness matrix. In some cases, $\gamma$ may be diagonal, and there may be zero $F_y$, but non-zero $F_x$ and $F_z$. The cross product of the medial-distal force may have a similar effect of the horizontal beam rotation (xz, zx)

In some cases, the total tooth rotation force may have components for each tooth and coupling components. For rotation of tooth 1, by Newton's $3^{rd}$ law the force may be:

$$F_{11} = \gamma(\theta_1 \times y_{12}), \text{ and } F_{21} = -\gamma(\theta_1 \times y_{12}).$$

For rotation of tooth 2, similarly the force may be:

$$F_{22} = \gamma(\theta_2 \times y_{21}), F_{12} = -\gamma(\theta_2 \times y_{21}) = \gamma(\theta_2 \times y_{12}).$$

The total force on tooth 1 may then be:

$$F_1 = \gamma((\theta_1 + \theta_2) \times y_{12}),$$

and the total force on tooth 2 may be:

$$F_2 = -F_1 = -\gamma((\theta_1 + \theta_2) \times y_{12}).$$

For the case of one tooth pair, because the total moment is zero, $$M_1' = M_2' = M' = F_2 \times \frac{y_{12}}{2} = -\gamma/2(\theta_1 + \theta_2) \times y_{12} \times y_{12}.$$

In the illustrated example, the cross product of the force in the extrusion direction may be quadratic. Based on the defined axes, $\theta_x$ gives $F_y$ and $\theta_y$ gives $F_x$, and they are opposite for the teeth of lower and upper jaws with the same rotation. The translation in the extrusion direction may not be represented by a linear model. Instead, the translation may be represented by $\theta \times z$ for both $\theta_1$ and $\theta_2$. In the illustrated embodiment, the force may be represented as:

$$F_1^C = \psi((\theta_1 - \theta_2) \times z) = -F_2^L,$$

where $\psi$ is a 3×3 stiffness diagonal matrix. In order to balance the force pair, another moment may be defined as:

$$M_1^C = M_2^C = \psi((\theta_1 - \theta_2) \times z) \times \frac{y_{12}}{2}.$$

As shown, if $\theta_1 = \theta_2$, the moment goes to zero.

To arrive at the total force, the forces on each teeth may be summed together, such that $$F_1 = 2\alpha T_{1,y} \hat{y} + \gamma((\theta_1 + \theta_2) \times y_{12}) + \psi((\theta_1 - \theta_2) \times z),$$

and because $F_2 = -F_1$. The total moment may then be expressed as:

$$M_1^L = \beta(\theta_1 - \theta_2) - \gamma/2(\theta_1 + \theta_2) \times y_{12} \times y_{12} + \psi((\theta_1 - \theta_2) \times z) \times \frac{y_{12}}{2}, \text{ and}$$

$$M_2^L = \beta(\theta_2 - \theta_1) - \gamma/2(\theta_1 + \theta_2) \times y_{12} \times y_{12} + \psi((\theta_1 - \theta_2) \times z) \times \frac{y_{12}}{2}.$$

Modeling Tooth Moments

Figure 6:
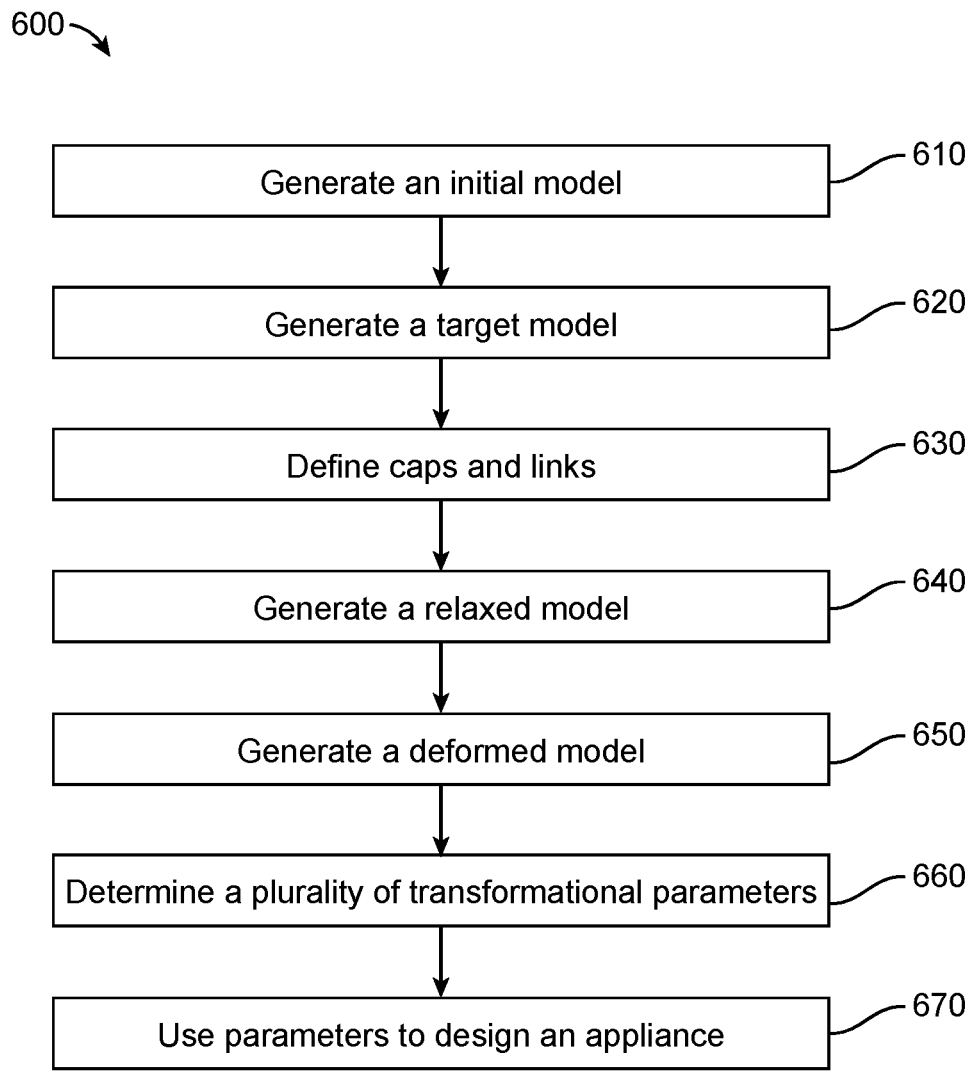
FIG. 6 illustrates a method for orthodontic modeling of tooth forces and/or moments, in accordance with one or more embodiments herein.

FIG. 6 illustrates a method 600 for orthodontic modeling of tooth movements. In some embodiments, the method 600 may comprise a portion of block 220 of a method 200. In other embodiments, the method 600 may be used to model a plurality of treatment stages and a plurality of treatment plans in order to determine an effectiveness of a treatment plan. In some cases, the method 600 may be applied as an operation in a method of digitally planning an orthodontic treatment method as described elsewhere herein. The method 600 may be applied to any of the treatment procedures described herein and may be performed by a suitable data processing system, such as for example the data processing system described in the section titled "Digital Processing System".

In block 610 of the method 600, an initial representation of the patient dentition may be generated. The initial representation of the patient dentition may comprise the arrangement of teeth before a stage in a treatment plan. In some embodiments, the initial representation may comprise the arrangement of teeth before starting a treatment plan. Systems and methods provided herein may comprise one or more representations of a patient dentition. A patient dentition may comprise an arrangement of teeth in a patient mouth. The arrangement of teeth may comprise the shape, location, morphology, number type, and/or physiological properties of one or more patient teeth. Dental information as described herein may comprise a patient dentition. A representation of a patient dentition may comprise an image of the patient's teeth. The image may be two-dimensional or three-dimensional.

The representation of the patient dentition before beginning treatment may be generated from a mold the patient's dental arch. For example, a practitioner (e.g. a dentist, an orthodontist, a technician, etc.) may make an impression of the subject's teeth and gingiva. Impressions may comprise impressions of the upper and/or the lower jaw. The impressions may be prepared using standard techniques, such as a dental tray filled with polyvinylsiloxane. The mold of the patient arch may then be scanned in order to generate a digital representation of the patient dentition.

The initial representation can be determined from a mold or a scan of the patient's teeth or mouth tissue, e.g., using wax bites, direct contact scanning, x-ray imaging, tomographic imaging, sonographic imaging, and other techniques for obtaining information about the position and structure of the teeth, jaws, gums and other orthodontically relevant tissue. From the obtained data, a digital data set can be derived that represents the initial (e.g., pretreatment) arrangement of the patient's teeth and other tissues.

In some cases, the teeth may be scanned or measured to determine the position of the teeth. Any appropriate technique may be used to scan the patient mouth. Such methods may include manual measurement, contact scanning, and non-contact scanning. Contact scanning may comprise actual or computer assisted measurement, including mechanical location devices. The teeth may be scanned by a non-contact method. In some examples, a non-contact method may comprise, but are not-limited too, laser scanning, optical scanning, CT scanning, ultrasound scanning, X-ray scanning, etc.

In some cases, multiple scanning steps may be combined in order to create a representation of the patient dentition. In some cases, multiple X-ray scans may be combined; multiple ultrasound scans, and/or multiple CT scans may be combined. In some cases, images may be digitized and/or analyzed to create a three dimensional representation of the patient dentition. The model may comprise a tomographic image of the patient dentition.

The scanning device may be coupled to a computer (e.g. a processor, a digital processing device, etc) as described elsewhere herein. Dental information, such as position and orientation for one or more of the patient teeth, may be obtained based on the scan of the patient mouth. The position and orientation information may be stored, analyzed, processed, and/or obtained from the scanner by the computer. The computer may act as a controller. The computer may comprise a plurality of computers which may be remote to one another each configured to execute one or more steps of the method described herein.

The dental information including the patient dentition may be collected over time, for example at each stage of a treatment plan. The position and orientation of the patient teeth may be recorded over time. The dental information may be used to assess the progress of a patient treatment plan. The dental information may be used to develop a patient treatment plan; however, in some cases, a patient treatment plan may be provided by another method.

In block 620 of the method 600, a target representation of the patient dentition may be generated. A target three dimensional representation may be generated. In some cases, the target representation comprises the target position of one or more patient teeth after a stage in the treatment plan. In some cases, the target dentition comprises the target arrangement of a patient teeth after the completion of a treatment plan. The treatment plan may be developed from a method described herein. Alternatively, the treatment plan may be provided from another method. In some cases, the treatment plan may be provided by a practitioner. The treatment plan may comprise one or a plurality of steps configured to adjust the alignment of the patient dentition toward a target arrangement. In some cases, the configuration of the orthodontic appliances herein can be determined according to a treatment plan for a patient, e.g., a treatment plan involving successive administration of a plurality of appliances for incrementally repositioning teeth.

The target representation may comprise the desired position of teeth at the end of a stage in a treatment plan. In some cases, the method includes a plurality of initial representations and target representations each representing the teeth at the beginning and end of a treatment stage in the treatment plan. In some examples, the treatment plan comprises greater than two stages. In some examples, the treatment plan comprises greater than 5 stages, greater than 10 stages, greater than 20 stages, greater than 100 stages or more. In some examples, the number of stages may be within a range defined by any two of the preceding values. In some cases the plurality of initial and final representations may be equal to the number of stages. The number of relaxed and deformed models may be equal to the number of stages in a treatment plan.

In some examples, computer-based treatment planning and/or appliance manufacturing methods can be used in order to facilitate the design and fabrication of appliances. For instance, one or more of the appliance components described herein can be digitally designed and fabricated with the aid of computer-controlled manufacturing devices (e.g., computer numerical control (CNC) milling, computer-controlled additive manufacturing such as 3D printing, etc.). In some embodiments, computer-based 3D planning/design tools, such as Treat™ software from Align Technology, Inc., may be used to design and fabricate the orthodontic appliances described herein.

At a block 630 of the method 600, a plurality of caps and a plurality of links may be defined. An operation in the method of modeling tooth moments may include separating each representation of the patient dentition into individual teeth. In some embodiments, each tooth has its own three-dimensional position and orientation. Each cap may represent a set of contact points on a tooth of the dentition. In some cases, each tooth may comprise a single cap. In some cases, a cap may represent more than one tooth. Two teeth may be represented with a single cap. Three teeth may be represented with a single cap. Each link may represent a connection between two of the caps. Each link may represent a connection between two adjacent caps. In other examples, each link may connect two non-adjacent caps. In some examples, the method may comprise defining a cap position and orientation for each tooth and a link, where each link connects neighboring adjacent caps. The plurality of caps and the plurality of links may define an aligner force response based on aligner deformation. The plurality of caps and plurality of links may represent the full patient dentition. In some cases, the plurality of caps and plurality of links may represent a portion of the patient dentition, for example, an upper arch, a lower arch, etc. In some cases, the plurality of caps and the plurality of links may represent only a portion of an arch.

At a block 640 of the method 600, a relaxed model may be generated. In some examples the method may comprise generating a relaxed model of a dental appliance from the plurality of caps and the plurality of links. The relaxed model may represent physical properties of the appliance at a first state. The first state may be an initial state. The relaxed model may represent the dental appliance. The relaxed model may represent the dental appliance in a first state. The relaxed model may represent an arrangement of caps and links which relates to the representation of the patient dentition after a stage of the treatment plan. Before the appliance is attached to a patient jaw, the appliance may be in a configuration that relates to the relaxed model of the aligner. Before application of the appliance on the patient teeth, the appliance may be in a relaxed and original manufactured shape. Before the application of the appliance on the patient teeth, the positions of the caps may be in relaxed positions.

At a block 650 of the method 600, a deformed model may be generated. In some examples the method may comprise generating a deformed model of a dental appliance from the plurality of caps and plurality of links. The deformed model may represent physical properties of the appliance at a second state. The second state may be a final state or an intermediate state. The second state may correspond to use of the dental appliance. The deformed model may represent the dental appliance. The deformed model may represent the dental appliance in a second state, for example, a state of the dental appliance in use. The deformed model may represent an arrangement of caps and links which relates to the representation of the patient dentition before a stage of the treatment plan. After the appliance is attached to a patient jaw and before progression of tooth movement, the appliance may be in a configuration that relates to the deformed model of the aligner. After application of the appliance on the patient teeth, the appliance may be in a deformed shape. The degree to which the appliance may be deformed may change as a function of time and as the teeth move. In some cases, the position of the deformed caps may be the same as the teeth positions, such as if the fit is perfect. In some cases, the position of the deformed caps may also be different by a bit, which effect may be limited by the stiffness and/or compliance of the appliance material. After the application of the appliance on the patient teeth, the positions of the caps may be in the deformed position.

At a block 660 of the method 600, a plurality of transformational parameters may be determined. The plurality of transformation parameters may comprise one or more of a plurality of forces and a plurality of moments. The plurality of transformational parameters may direct a patient dentition from the initial model to the target model. In some embodiments, the transformational parameters may comprise one or more forces. In some embodiments, the transformational parameters may comprise one or more moments. The transformation parameters may comprise forces and moments. The plurality of transformation parameters may relate to forces and moments for each tooth. In some embodiments, the force and moment between any two neighboring caps may be nonlinearly related to the translational and rotational movement. The nonlinear parts may include but are not limited to the cross products of the rotation vector and the distance vector between two teeth or the teeth direction. A force system can include one or more forces and/or one or more torques. Different force systems can result in different types of tooth movement, such as tipping, translation, rotation, extrusion, intrusion, root movement, etc. Determination of the force system can be performed in a variety of ways. For example, in some embodiments, the force system is determined on a patient-by-patient basis, e.g., using patient-specific data.

At a block 670 of the method 600, the plurality of dental parameters may be used to design a dental appliance. Having a set of moments and forces for the motion of each tooth, an appliance may be generated which produces or approximates the production of the calculated force. In some embodiments, the aligner tooth receiving cavities are in positions and orientations that correspond to the position and orientation of the caps in the model. In some embodiments, the motions and forces are configured to move the teeth in the quickest fashion with the least amount of round-tripping to bring the teeth from their initial positions to their desired target positions. In this way, the stage can constitute a clinically viable repositioning, and the aggregate of stages can constitute a clinically viable sequence of tooth positions.

In some embodiments, an appliance geometry and/or material composition for an orthodontic appliance configured to produce the force system may be determined. The appliance can be any embodiment of the appliances discussed herein, such as an appliance having variable localized properties, integrally formed components, and/or power arms.

Although the above blocks show a method 600 of orthodontic modeling of tooth movements in accordance with some embodiments, a person of ordinary skill in the art will recognize some variations based on the teaching described herein. Some of the blocks may comprise sub-blocks. Some of the blocks may be repeated as often as desired. One or more blocks of the method 600 may be performed with any suitable fabrication system or device, such as the embodiments described herein. Some of the blocks may be optional, and the order of the blocks can be varied as desired.

In some embodiments, the method 600 may be used for optimizing the predictability of patient treatment. The method may be used to predict mesial distal root control. The method may be used to predict optimized treatment plans with less processing power. The method may be used be used to predict the viability of a treatment plan. The method may be used to evaluate the progress of a treatment plan. The method may be used to approximate force values which may be more easily manufactured, such as for example, optimizing material properties in multi-material direct manufacturing.

Digital Processing System

Figure 7:
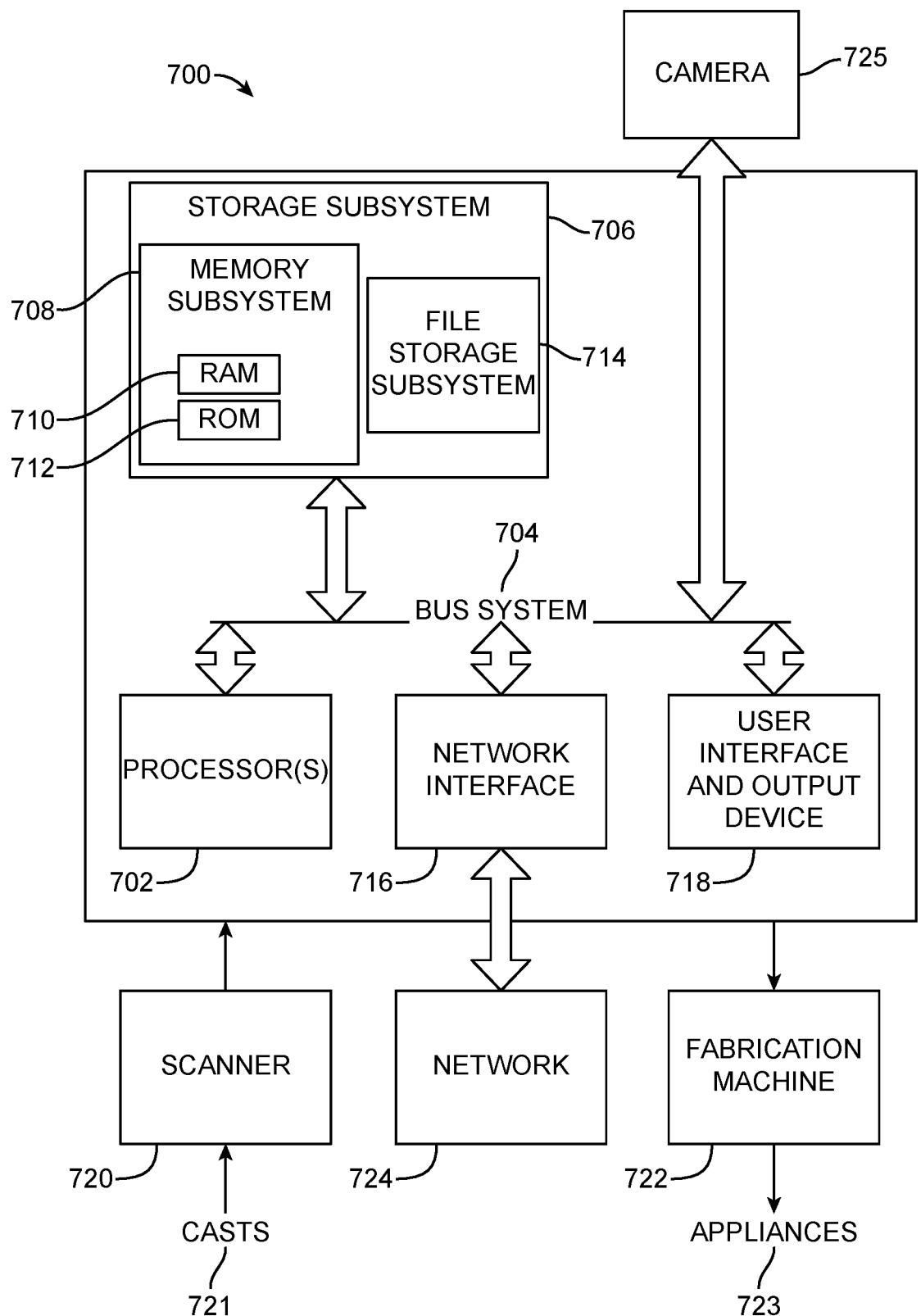
FIG. 7 is a simplified block diagram of a system for designing an orthodontic appliance and planning an orthodontic treatment, in accordance with one or more embodiments herein.

FIG. 7 is a simplified block diagram of a data processing system 700 that may be used in executing methods and processes described herein. The data processing system 700 typically includes at least one processor 702 that communicates with one or more peripheral devices via bus subsystem 704. These peripheral devices typically include a storage subsystem 706 (memory subsystem 708 and file storage subsystem 714), a set of user interface input and output devices 718, and an interface to outside networks 716. This interface is shown schematically as "Network Interface" block 716, and is coupled to corresponding interface devices in other data processing systems via communication network interface 724. Data processing system 700 can include, for example, one or more computers, such as a personal computer, workstation, mainframe, laptop, and the like.

The user interface input devices 718 are not limited to any particular device, and can typically include, for example, a keyboard, pointing device, mouse, scanner, interactive displays, touchpad, joysticks, etc. Similarly, various user interface output devices can be employed in a system of the invention, and can include, for example, one or more of a printer, display (e.g., visual, non-visual) system/subsystem, controller, projection device, audio output, and the like.

Storage subsystem 706 maintains the basic required programming, including computer readable media having instructions (e.g., operating instructions, etc.), and data constructs. The program modules discussed herein are typically stored in storage subsystem 706. Storage subsystem 706 typically includes memory subsystem 708 and file storage subsystem 714. Memory subsystem 708 typically includes a number of memories (e.g., RAM 710, ROM 712, etc.) including computer readable memory for storage of fixed instructions, instructions and data during program execution, basic input/output system, etc. File storage subsystem 714 provides persistent (non-volatile) storage for program and data files, and can include one or more removable or fixed drives or media, hard disk, floppy disk, CD-ROM, DVD, optical drives, and the like. One or more of the storage systems, drives, etc., may be located at a remote location, such coupled via a server on a network or via the internet/World Wide Web. In this context, the term "bus subsystem" is used generically so as to include any mechanism for letting the various components and subsystems communicate with each other as intended and can include a variety of suitable components/systems that would be known or recognized as suitable for use therein. It will be recognized that various components of the system can be, but need not necessarily be at the same physical location, but could be connected via various local-area or wide-area network media, transmission systems, etc.

Scanner 720 includes any means for obtaining a digital representation (e.g., images, surface topography data, etc.) of a patient's teeth (e.g., by scanning physical models of the teeth such as casts 721, by scanning impressions taken of the teeth, or by directly scanning the intraoral cavity), which can be obtained either from the patient or from treating professional, such as an orthodontist, and includes means of providing the digital representation to data processing system 700 for further processing. Scanner 720 may be located at a location remote with respect to other components of the system and can communicate image data and/or information to data processing system 700, for example, via a network interface 724. Fabrication system 722 fabricates appliances 723 based on a treatment plan, including data set information received from data processing system 700. Fabrication machine 722 can, for example, be located at a remote location and receive data set information from data processing system 700 via network interface 724. The camera 725 may include any image capture device configured to capture still images or movies. The camera 725 may facilitate capturing various perspectives of a patient's dentition. In some implementations, the camera 725 may facilitate capture of images at various focal lengths and distances from the patient.

The data processing aspects of the methods described herein can be implemented in digital electronic circuitry, or in computer hardware, firmware, software, or suitable combinations thereof. Data processing apparatus can be implemented in a computer program product tangibly embodied in a machine-readable storage device for execution by a programmable processor. Data processing blocks can be performed by a programmable processor executing program instructions to perform functions by operating on input data and generating output. The data processing aspects can be implemented in one or more computer programs that are executable on a programmable system, the system including one or more programmable processors operably coupled to a data storage system. Generally, a processor will receive instructions and data from a read-only memory and/or a random access memory. Storage devices suitable for tangibly embodying computer program instructions and data include all forms of nonvolatile memory, such as: semiconductor memory devices, such as EPROM, EEPROM, and flash memory devices; magnetic disks such as internal hard disks and removable disks; magneto-optical disks; and CD-ROM disks.

EXAMPLES

The following examples show exemplary use cases for the methods disclosed herein. While examples, shown using 2, 3, or 4 teeth, the model may be extended to full arch modeling as described elsewhere herein.

Two Teeth with Equal Rotation

Figure 8:
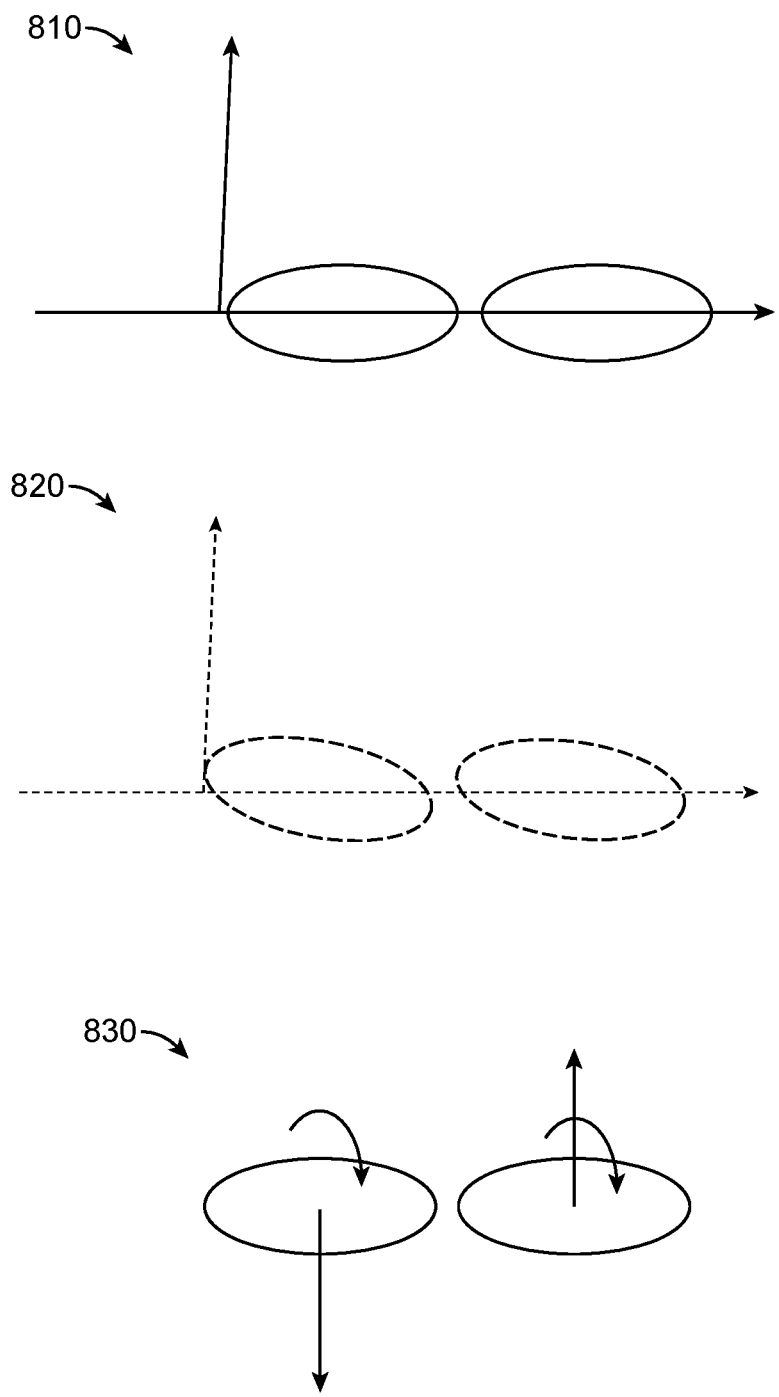
FIG. 8 illustrates an example of a moment model of a pair of teeth with equal rotation, in accordance with one or more embodiments herein.

FIG. 8 illustrates an example of a moment model of a pair of teeth with equal rotation. The relaxed model 810 is shown, and the deformed model 820 is shown. Similar to the embodiment shown herein above, the linear parts may all be zero. By definition, $\theta_{2z}=\theta_{1z}=\theta_z$, and the distance between the two teeth is y. The quadratic parts may then be expressed as:

$$F_{1x}=-F_{2x}=-\gamma 2\theta_z y.$$

The moments may be expressed as:

$$M'_{1z} = M'_{2z} = -\frac{\gamma}{2}(\theta_1 + \theta_2) \times y_{12} \times y_{12} = \gamma \theta_z y^2.$$

$\theta_X$ may be expressed similarly. A force diagram 830 is shown. The arrows indicate the direction of the forces, straight arrows, and moments, curved arrows on each tooth.

Three Teeth with Equal Rotation

Figure 9A:
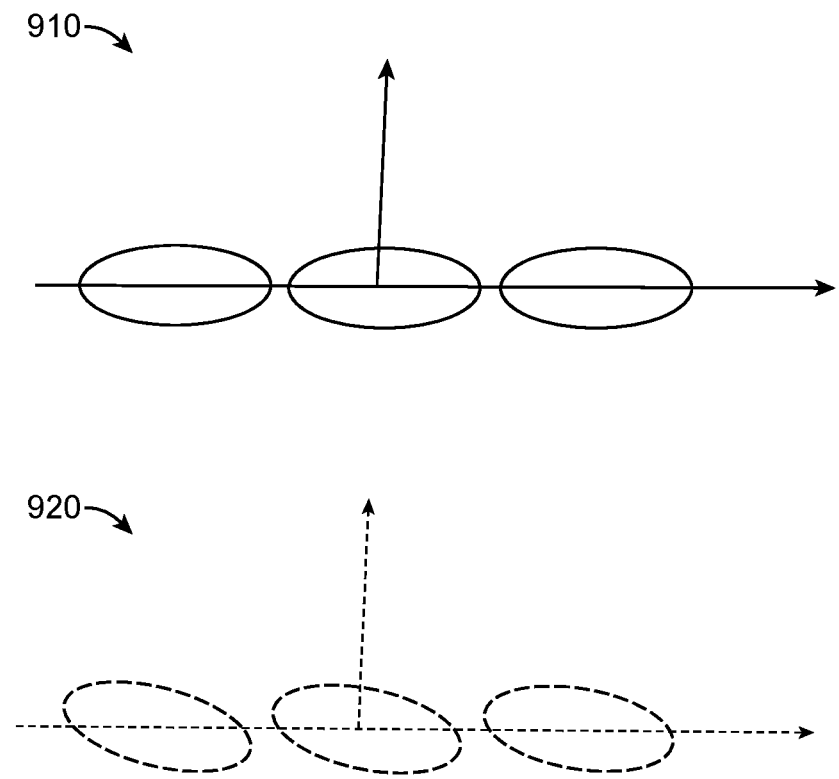
FIG. 9A illustrates an example of a moment model of three teeth with equal rotation, in accordance with one or more embodiments herein.

FIG. 9A illustrates an example of a moment model of three teeth with equal rotation. The relaxed model 910 is shown, and the deformed model 920 is shown. In the illustrated example, all teeth may be in a line and may rotate in z with angle θ and separation distance y. Similar to the previous example, the linear parts may be zero and the quadratic part survives.

Figure 9B:
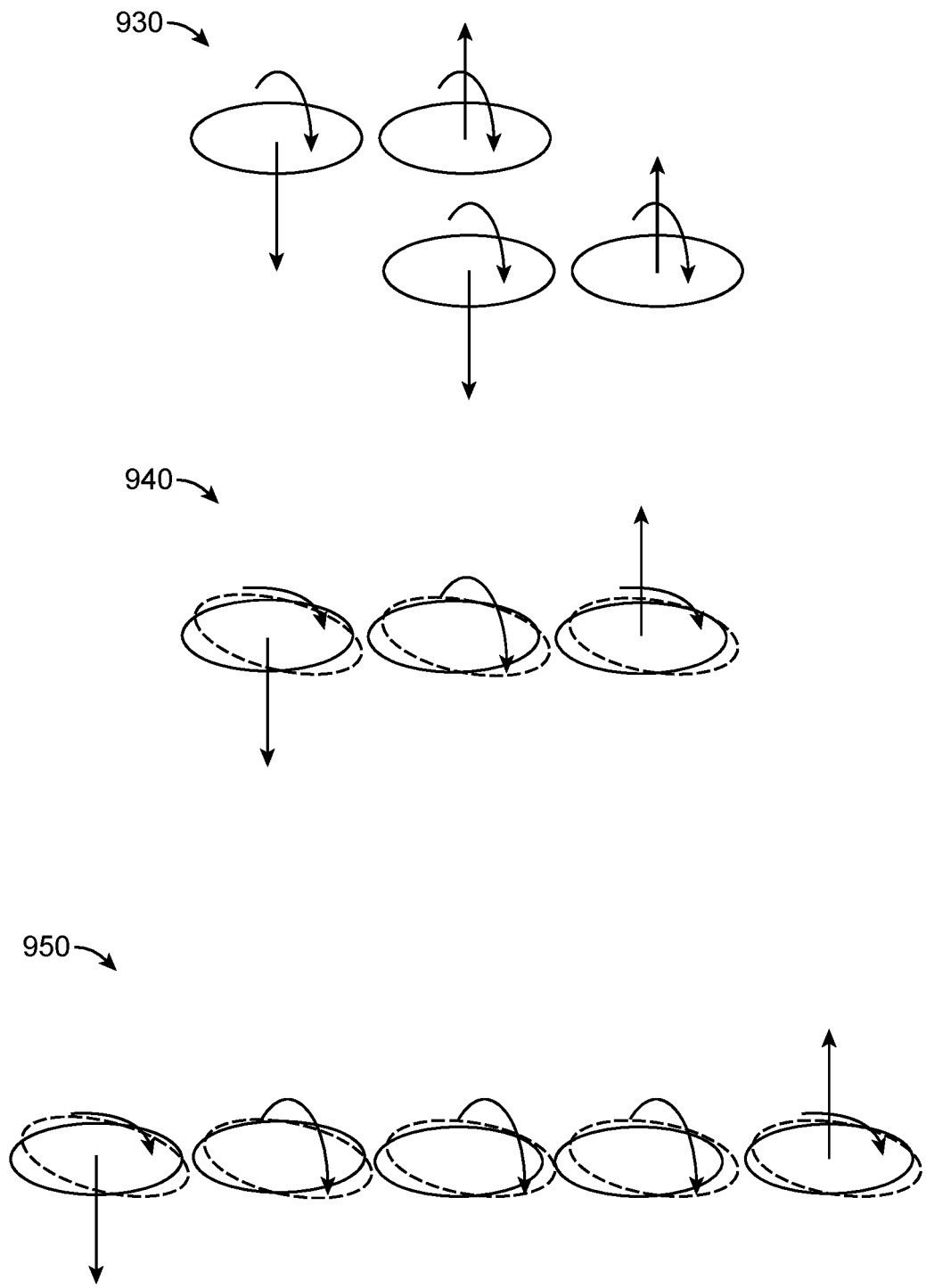
FIG. 9B illustrates the moment model of FIG. 9A where the teeth may be broken into two pairs with a force and moment on each tooth, in accordance with one or more embodiments herein.

As shown in FIG. 9B, the teeth may be broken into two pairs 930 with a force and moment on each tooth. In the example and using the result from the previous example, the force on tooth left from right (F1) may be defined as:

$$F_{12x}=F_{23x}=-\gamma 2\theta y,$$

and the force on tooth right from left (F2) may be defined as:

$$F_{21x}=F_{32x}=\gamma 2\theta y.$$

In the example and using the result from above, the moment on tooth left from right (M1) may be defined as:

$$M_{12z}=M_{23z}=\gamma\theta y^2,$$

and the moment on the tooth right from left (M2) may be defined as:

$$M_{21z}=M_{32z}=\gamma\theta y^2.$$

A force diagram 940 comprising the sum of the forces on each pair is shown. In the example, the total force may be $$F_{1x}=-F_{3x}=-\gamma 2\theta y$$

and $F_2=0$. Similarly, the total moment may be $$M_{1z}=M_{3z}=\gamma\theta y^2,$$

and $M_{2z}=2\gamma\theta y^2$. As shown, the middle tooth may only experience rotation and no force. The example with 4 or more teeth may be derived similarly, and a force diagram is shown 950. Rotation in x may be derived similarly.

Middle Tooth Vertical Translation

Figure 10A:
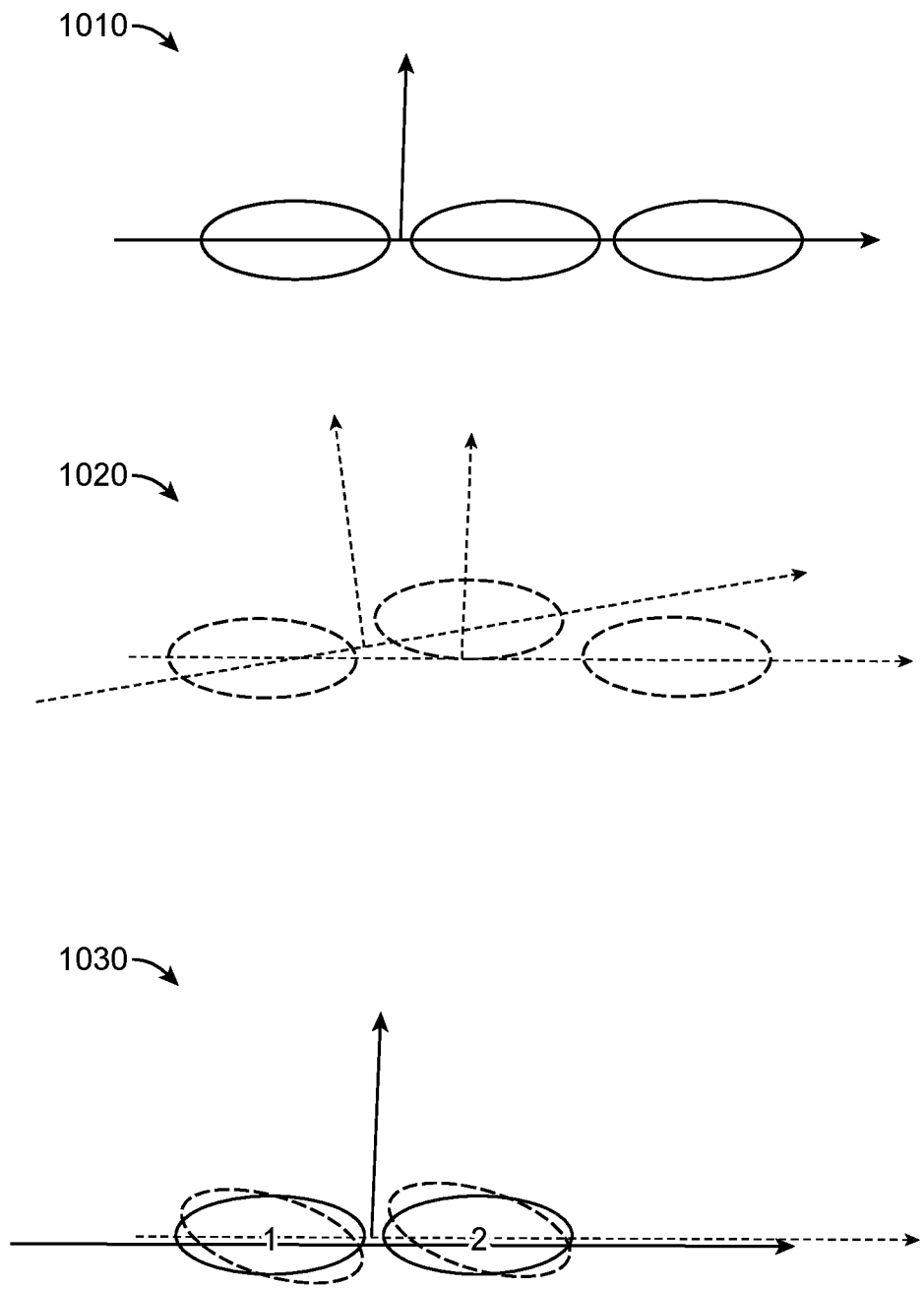
FIG. 10A illustrates an example of a moment model of three teeth with vertical displacement of the middle tooth, in accordance with one or more embodiments herein.

FIG. 10A illustrates an example of a moment model of three teeth with vertical displacement of the middle tooth. The relaxed model 1010 is shown, and the deformed model 1020 is shown. In the illustrated example, the translation in the x direction $T_x=t$, and the distance between the two teeth is y. Y translation can be represented as $$\delta=\sqrt{y^2+t^2}-y\sim t^2/2,$$

and Z rotation can be represented as $$\theta = \arctan\frac{t}{y}.$$

A map of the relaxed to the deformed model for the left pair 1030 is shown.

Figure 10B:
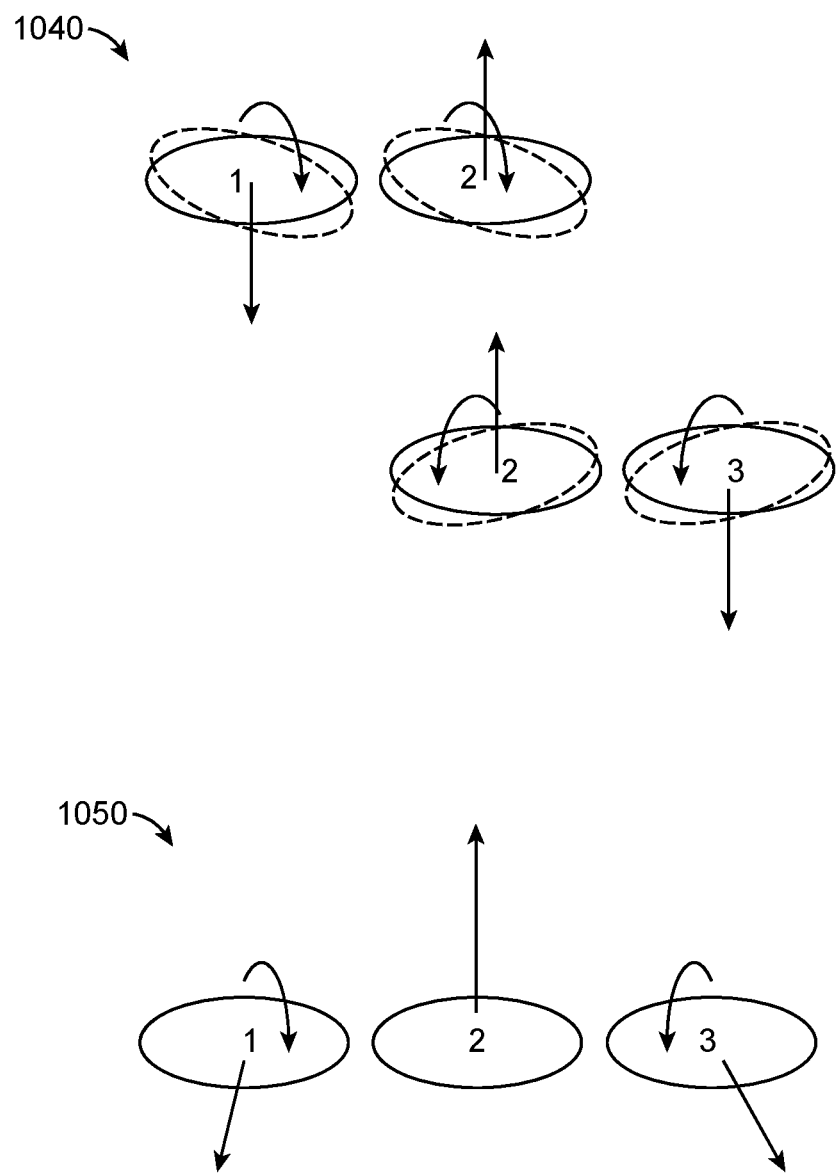
FIG. 10B illustrates the moment model of FIG. 10A where the teeth may be broken into two pairs with a force and moment on each tooth, in accordance with one or more embodiments herein.

As shown in FIG. 10B, the teeth may be broken into two pairs 1040 with a force and moment on each tooth. In the example, the force from y translation may be:

$$F_{21y}=-F_{12y}=\alpha\delta,$$

and from z rotation:

$$F_{21x}=-F_{12x}=\gamma 2\theta y.$$

Similarly, the moment may be $$M_{12z}=M_{21z}=\gamma\theta y^2.$$

Similarly for T2 to T3, Z rotation may be $$-\theta = -\arctan\frac{t}{d}.$$

Therefore, $F_{32y}=-F_{23y}=\alpha\delta$, $-F_{32x}=F_{23x}=\gamma 2\theta y$, and $M_{32z}=M_{23z}=-\gamma\theta y^2$.

A force diagram 1050 comprising the sum of the forces on each pair is shown. The total force on tooth 2 may be expressed as:

$$F_2=F_{23x}+F_{21x}=4\gamma\theta y\hat{x},$$

and the moment $M_{2z}=0$. The total force on tooth 1 may be expressed as:

$$F_1=-\alpha\delta\hat{y}-\gamma 2\theta y\hat{x},$$

and the moment as:

$$M_{1z}=\gamma\theta d^2=-M_{3z}.$$

The force on tooth 3 may be expressed as:

$$F_3=\alpha\delta\hat{y}-\gamma 2\theta y\ \hat{x}.$$

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A computer-implemented method for digital treatment planning, the computer-implemented method comprising:
   defining a plurality of caps, wherein each cap of the plurality of caps represents a set of contact points on a tooth of a patient's dentition;
   defining a plurality of links, wherein each link of the plurality of links represents a connection between a pair of the plurality of caps;
   generating a relaxed model of a dental appliance using the plurality of caps and the plurality of links, wherein the relaxed model represents physical properties of the dental appliance prior to use by the patient;
   generating a deformed model of the dental appliance using the plurality of caps and plurality of links, wherein the deformed model of the dental appliance represents physical properties of the dental appliance after use by the patient; and
   transforming the relaxed model to the deformed model to direct the patient dentition towards a target tooth arrangement,
   wherein the plurality of caps and the plurality of links are defined at least in part based on an initial three-dimensional model of the patient's dentition; wherein the initial three-dimensional model of the patient's dentition is collected from an intraoral scan of the patient's mouth.

2. The method of claim 1, further comprising generating a target three-dimensional model of the patient's dentition, the target three-dimensional model representing the patient's dentition at the target tooth arrangement.

3. The method of claim 1, wherein each of the plurality of links comprises a Hookian stiffness parameter.

4. The method of claim 1, further comprising mapping the relaxed model onto the deformed model.

5. The method of claim 4, further comprising expressing the relaxed model and the deformed model in an elastic coordinate system.

6. The method of claim 1, further comprising generating a plurality of treatment plans and selecting the target treatment plan from the plurality of treatment plans based on treatment outcomes of the plurality of treatment plans.

7. The method of claim 1, wherein transforming the relaxed model to the deformed model comprises determining a plurality of transformational parameters.

8. The method of claim 7, wherein the plurality of transformation parameters comprise one or more of a plurality of forces and a plurality of moments.

9. The method of claim 1, wherein the method reduces time for generating a force model by at least about 10% relative to solid model analysis.

10. A non-transitory computing device readable medium storing instructions executable by a processor to cause a computing device to perform a method for digital treatment planning, the method comprising:
    defining a plurality of caps, wherein each cap of the plurality of caps represents a set of contact points on a tooth of a patient's dentition;
    defining a plurality of links, wherein each link of the plurality of links represents a connection between a pair of the plurality of caps;
    generating a relaxed model of a dental appliance using the plurality of caps and the plurality of links, wherein the relaxed model represents physical properties of the dental appliance prior to use by the patient;
    generating a deformed model of the dental appliance using the plurality of caps and plurality of links, wherein the deformed model of the dental appliance represents physical properties of the dental appliance after use by the patient; and
    transforming the relaxed model to the deformed model to direct the patient dentition towards a target tooth arrangement,
    wherein the plurality of caps and the plurality of links are defined at least in part based on an initial three-dimensional model of the patient's dentition; wherein the initial three-dimensional model of the patient's dentition is collected from an intraoral scan of the patient's mouth.

11. The non-transitory computing device readable medium of claim 10, wherein the method further comprises generating a target three-dimensional model of the patient's dentition, the target three-dimensional model representing the patient's dentition at the target tooth arrangement.

12. The non-transitory computing device readable medium of claim 10, wherein each of the plurality of links comprises a Hookian stiffness parameter.

13. The non-transitory computing device readable medium of claim 10, wherein the method further comprises mapping the relaxed model onto the deformed model.

14. The non-transitory computing device readable medium of claim 10, wherein the method further comprises expressing the relaxed model and the deformed model in an elastic coordinate system.

15. The non-transitory computing device readable medium of claim 10, wherein the method further comprises generating a plurality of treatment plans and selecting the target treatment plan from the plurality of treatment plans based on treatment outcomes of the plurality of treatment plans.

16. The non-transitory computing device readable medium of claim 10, wherein transforming the relaxed model to the deformed model comprises determining a plurality of transformational parameters.

17. The non-transitory computing device readable medium of claim 16, wherein the plurality of transformation parameters comprise one or more of a plurality of forces and a plurality of moments.

18. The non-transitory computing device readable medium of claim 10, wherein the method reduces time for generating a force model by at least about 10% relative to solid model analysis.

* * * * *